(12) United States Patent
Sutoko et al.

(10) Patent No.: US 11,331,048 B2
(45) Date of Patent: May 17, 2022

(54) BRAIN CONNECTIVITY ANALYSIS SYSTEM AND BRAIN CONNECTIVITY ANALYSIS METHOD

(71) Applicant: HITACHI, LTD., Tokyo (JP)

(72) Inventors: Stephanie Sutoko, Tokyo (JP); Masashi Kiguchi, Tokyo (JP); Atsushi Maki, Tokyo (JP); Tsukasa Funane, Tokyo (JP); Hiroki Sato, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1030 days.

(21) Appl. No.: 15/723,605

(22) Filed: Oct. 3, 2017

(65) Prior Publication Data
US 2018/0098738 A1    Apr. 12, 2018

(30) Foreign Application Priority Data

Oct. 12, 2016    (JP) .............................. JP2016-201200

(51) Int. Cl.
| | |
|---|---|
| *A61B 5/00* | (2006.01) |
| *G16H 40/63* | (2018.01) |
| *G16H 10/60* | (2018.01) |
| *G16H 50/50* | (2018.01) |
| *A61B 5/369* | (2021.01) |

(52) U.S. Cl.
CPC ............ *A61B 5/7275* (2013.01); *A61B 5/369* (2021.01); *A61B 5/4064* (2013.01); *A61B 5/742* (2013.01); *A61B 5/743* (2013.01); *A61B 5/7475* (2013.01); *G16H 10/60* (2018.01); *G16H 40/63* (2018.01); *G16H 50/50* (2018.01)

(58) Field of Classification Search
CPC ... A61B 5/7275; A61B 5/0476; A61B 5/7475; A61B 5/743; A61B 5/742; A61B 5/4064; G16H 50/50; G16H 40/63; G16H 10/60
See application file for complete search history.

(56) References Cited

U.S. PATENT DOCUMENTS

| | | | |
|---|---|---|---|
| 2013/0113816 A1 | 5/2013 | Sudarsky et al. | |
| 2013/0245485 A1* | 9/2013 | Mashour | A61B 5/74 600/544 |
| 2014/0222738 A1 | 8/2014 | Joyce et al. | |
| 2014/0296691 A1* | 10/2014 | Kawasaki | A61B 5/4064 600/407 |
| 2015/0018664 A1* | 1/2015 | Pereira | A61B 5/4064 600/410 |

* cited by examiner

*Primary Examiner* — Devin B Henson
*Assistant Examiner* — Joseph A Tombers
(74) *Attorney, Agent, or Firm* — Mattingly & Malur, PC

(57) ABSTRACT

Provided is a technique for comprehensively understanding the relationship between brain regions. A brain connectivity analysis system herein includes a memory configured to have stored therein a connectivity analysis program for analyzing the connectivity; and a processor configured to read the connectivity analysis program from the memory and analyze the connectivity. The processor is configured to execute a process of acquiring from a storage unit measured data on a plurality of selected regions of a brain, a process of determining at least two of the plurality of regions as seed regions and calculating a plurality of connectivity features for the seed regions and other regions from the measured data on the plurality of regions, and a process of generating a connectivity feature graph showing a relationship between a transfer delay time and another connectivity feature of each region that are included in the plurality of connectivity features.

14 Claims, 16 Drawing Sheets

Correlation Strength-Delay Time Feature   Distance-Delay Time Feature   Multiple-Variable Feature

FIG. 4

Command Input: 301

Analysis Type 302

☐ Personal Analysis  ☑ Group Analysis — 301b

Data Selection
More than 1 data can be selected.

Group 1: — 401  — 405  — 406

| Name: — 404 | Gender | Age |
|---|---|---|
| 2016xxxx_idxxxxx1 | F | 25 |
| 2016xxxx_idxxxxx2 | M | 32 |
| 2016xxxx_idxxxxx3 | M | 29 |
| 2016xxxx_idxxxxx4 | F | 29 |

Group 2 (Comparison Target): — 402  — 405  — 406

| Name: — 404 | Gender | Age |
|---|---|---|
| 2016xxxx_idxxxxx1 | F | 25 |
| 2016xxxx_idxxxxx2 | M | 32 |
| 2016xxxx_idxxxxx3 | M | 29 |
| 2016xxxx_idxxxxx4 | F | 29 |

☑ Select All Analysis Methods — 308a

Connectivity Motif Analysis Selection — 307
More than 1 analysis method can be selected.

Analysis method — 308b
☑ Area under curve — 309
☑ Distribution type — 310
☑ Skewness — 311

[ Advanced Settings ] — 314  [ OK ] — 315  [ Reset ] — 316

— 40

BRAIN CONNECTIVITY ANALYSIS SYSTEM AND BRAIN CONNECTIVITY ANALYSIS METHOD

CROSS REFERENCE TO RELATED APPLICATIONS

The present application claims priority from Japanese patent application JP 2016-201200 filed on Oct. 12, 2016, the content of which is hereby incorporated by reference into this application.

BACKGROUND

Technical Field

The present disclosure relates to a brain connectivity analysis system and a brain connectivity analysis method.

Background Art

Research for identifying connectivity (which includes both functional and effective connectivity) between brain regions has been widely conducted. However, since connectivity between brain regions is complex, it is difficult to analyze information on connectivity features like network attributes and display such information.

Regarding visualization of brain network connectivity, US 2013/0113816 A, for example, discloses displaying brain connectivity on a screen using a method of predicting the relationship between nodes of brain regions using a tree structure and a method of displaying bundled edges through 2D visualization. In addition, US 2014/0222738 A, for example, discloses providing an agent-based brain model using an analysis method (functional MRI) based on functional connectivity.

SUMMARY

However, the methods of the two references mentioned above are intended to analyze connectivity between only local brain regions, and not connectivity between the entire brain regions. Therefore, with the techniques disclosed in such references, it would be impossible to comprehensively understand the relationship (connectivity) between brain regions.

The present disclosure has been made in view of the foregoing circumstances, and provides a technique for comprehensively understanding the relationship between brain regions.

Accordingly, a brain connectivity analysis system in accordance with the present disclosure includes a memory configured to have stored therein a connectivity analysis program for analyzing the connectivity; and a processor configured to read the connectivity analysis program from the memory and analyze the connectivity. The processor is configured to execute a process of acquiring from a storage unit measured data on a plurality of selected regions of a brain, a process of determining at least one of the plurality of regions as a seed region and calculating a plurality of connectivity features for the seed region and another region from the measured data on the plurality of regions, and a process of generating a connectivity feature graph showing a relationship between a transfer delay time and another connectivity feature of each region that are included in the plurality of connectivity features.

Further features related to the present disclosure will become apparent from the description of the specification and the accompanying drawings. In addition, embodiments of the present disclosure can be implemented by elements, a combination of a variety of elements, the following detailed description, and the appended claims.

The description of the specification contains only typical illustrative examples. Therefore, claims or examples of the application of the present disclosure should not be limited in any sense.

According to the present disclosure, a technique for comprehensively understanding the relationship between brain regions is provided.

BRIEF DESCRIPTION OF THE DRAWINGS

FIG. 4 is a diagram showing a command input screen 40 when an operator selects group analysis 301b as the analysis type 301;

DETAILED DESCRIPTION

Figure 1:
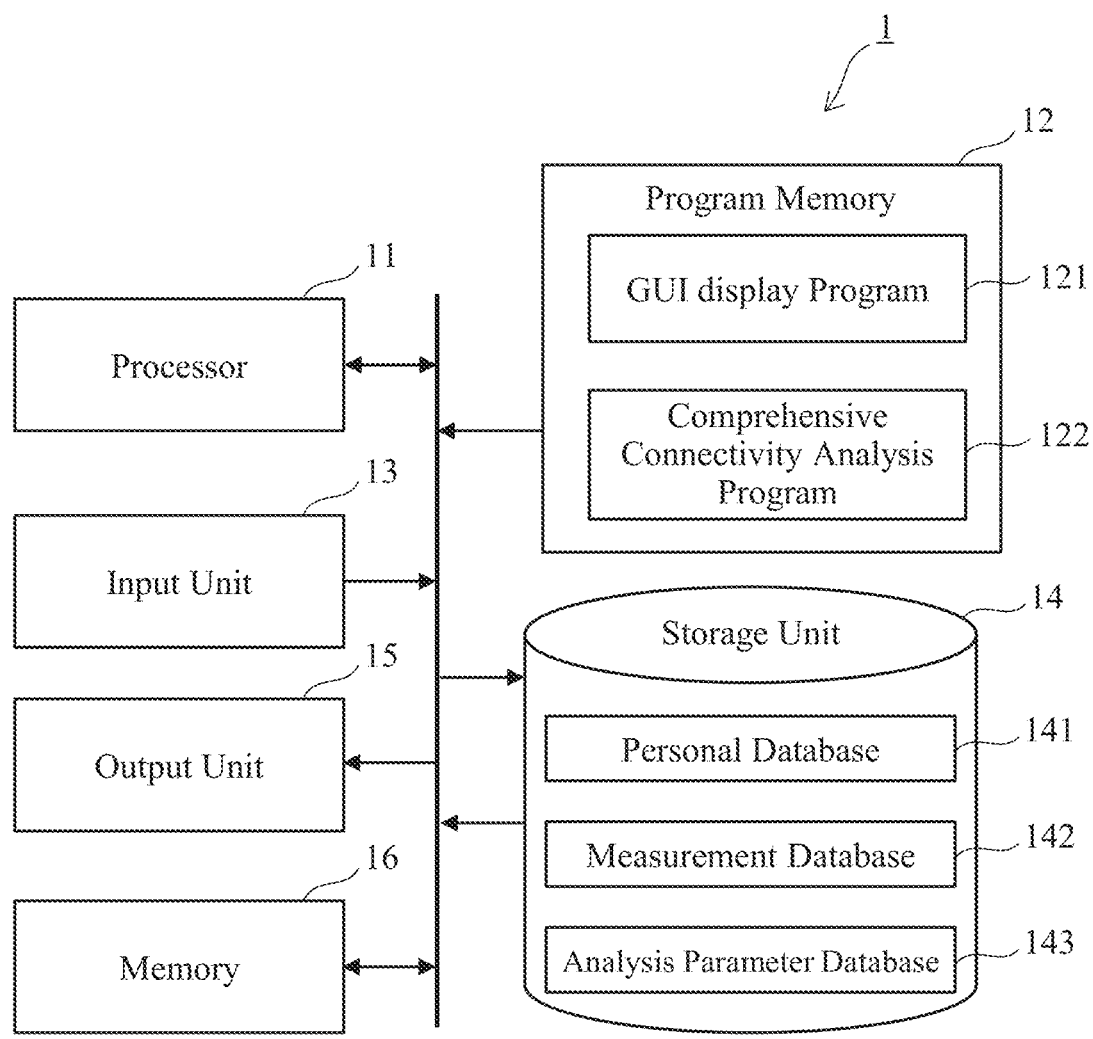
FIG. 1 is a diagram showing the schematic configuration of a brain connectivity analysis system (also referred to as a diagnosis assisting device, a diagnosis assisting system, a brain connectivity information presentation device, a brain connectivity information presentation system, or the like) 1 in accordance with an embodiment of the present disclosure.

A brain connectivity analysis system in accordance with an embodiment of the present disclosure is adapted to calculate connectivity (for example, correlation strength, information transfer delay time, information transfer direction, and distance between channels (regions)) between a plurality of channels (regions) selected by an operator and display the calculation results as global connectivity features on a screen of a display device.

Hereinafter, embodiments of the present disclosure will be described with reference to the accompanying drawings. In the drawings, elements that are functionally the same may be denoted by the same reference numerals. Although the drawings illustrate specific embodiments and implementations in accordance with the principle of the present disclosure, such embodiments and implementations are only for understanding of the present disclosure and should not be used to narrowly construe the present disclosure.

The following embodiments will be described in full detail for those skilled in the art to carry out the present disclosure. However, it should be noted that other implementations and embodiments are also possible and any changes in the configuration or structure as well as replacement of a variety of elements is possible within the spirit and scope of the present disclosure. Therefore, the following description should not be constructed by being limited to such implementations or embodiments.

Further, the embodiments of the present disclosure can be implemented by software that runs on a general-purpose computer, hardware, or a combination of both.

Although the following description illustrates each information of the present disclosure in a "table" format, such information need not necessarily be represented by a data structure of a table, and may also be represented by other data structures such as a list, DB (database), and cue. Therefore, in order to show that such information does not depend on its data structure, all of a "table," list," "DB," "cue," and the like may simply be called "information."

<Configuration of Brain Connectivity Analysis System>

FIG. 1 is a diagram showing the schematic configuration of a brain connectivity analysis system (also referred to as a diagnosis assisting device, a diagnosis assisting system, a brain connectivity information presentation device, or a brain connectivity information presentation system) 1 in accordance with an embodiment of the present disclosure.

The brain connectivity analysis system 1 can be constructed from a common computer, and includes a processor 11, such as a CPU or a MPU; a program memory 12 having stored therein a GUI display program 121, a comprehensive connectivity analysis program 122, and a variety of other programs; an input unit 13; a storage unit 14; an output unit 15; and a memory 16.

The storage unit 14 includes a personal database 141 having stored therein data or information on each patient, a measurement database (data on a population) 142 having stored therein each measured biological data (a measured brain wave signal of each patient, such as scan data obtained through MRI or optical topography data, for example), and an analysis parameter database 143 having stored therein analysis parameters.

The input unit 13 includes a device used for an operator to input a command or information into the brain connectivity analysis system 1, such as a keyboard, a mouse, a touch panel, a variety of switches, and a microphone, for example. In this embodiment, an operator (user) inputs a variety of commands in accordance with GUIs shown in FIGS. 3 to 6 using the input unit 13.

The output unit 15 includes a device used to output analysis results, such as a display device or a speaker, for example.

The processor 11 reads the GUI display program 121 and the comprehensive connectivity analysis program 122 (which correspond to programs in the flowchart of FIG. 7) from the program memory 12 into an internal memory (not shown) of the processor 11, and executes them.

The processor 11 executes the GUI display program 121 and forms a GUI (graphical user interface) for an operator to input a command, and also displays a GUI configured as a display screen of the output unit (display device) 15.

The processor 11 processes a measured biological signal using the comprehensive connectivity analysis program 122 to comprehensively analyze connectivity between brain regions. In order to analyze connectivity between brain regions using a measured biological signal, the processor 11 reads the data stored in the personal database 141 or the measurement database 142 of the storage unit 14 as well as analysis parameters stored in the analysis parameter database 143 in response to a variety of commands input by a user, and then processes the measured biological signal to comprehensively analyze connectivity between brain regions.

The comprehensive connectivity analysis program 122 is adapted to perform a process of converting the current measured data into an index using the measured data and the data stored in the storage unit. As described below with reference to FIG. 7, which index is to be used is input by a doctor or an operator via the input unit 13.

<Regarding Database>

The personal database 141 is a database having stored therein personal information on each subject (for example, a patient or healthy subject), and can contain as constituent items the subject ID for uniquely identifying and distinguishing the subject, the name of the subject (the patient or healthy subject), the age of the subject, and the gender of the subject, for example.

The measurement database 142 is a database having stored therein data associated with measured data on each subject, and can contain as constituent items the subject ID, the measurement date, and a measured biological signal of each brain region of the subject, for example.

The analysis parameter database 143 is a database having stored therein parameters for use in preprocessing data and parameters for executing a variety of analysis methods, for example. Examples of the parameters for use in preprocessing data include a body motion removal value indicating the amplitude value for removing a body motion, a high-pass filter coefficient for removing low-frequency components of a measured biological signal, a low-pass filter coefficient for removing high-frequency components of a measured biological signal, a smoothing coefficient indicating the coefficient of a smoothing filter, and a noise correction target indicating a target for noise correction. Examples of the parameters for executing a variety of analysis methods include arithmetic expressions or parameters for executing analyses of the area under the distribution curve (area under curve), distribution type, skewness, kurtosis, and the number of peaks.

Such databases are stored in the storage unit 14 included in the computer of the brain connectivity analysis system 1, but may also be stored in a server or the like that is remotely connected to the system over a network (not shown).

<Exemplary Arrangement of Probe>

Figure 2:
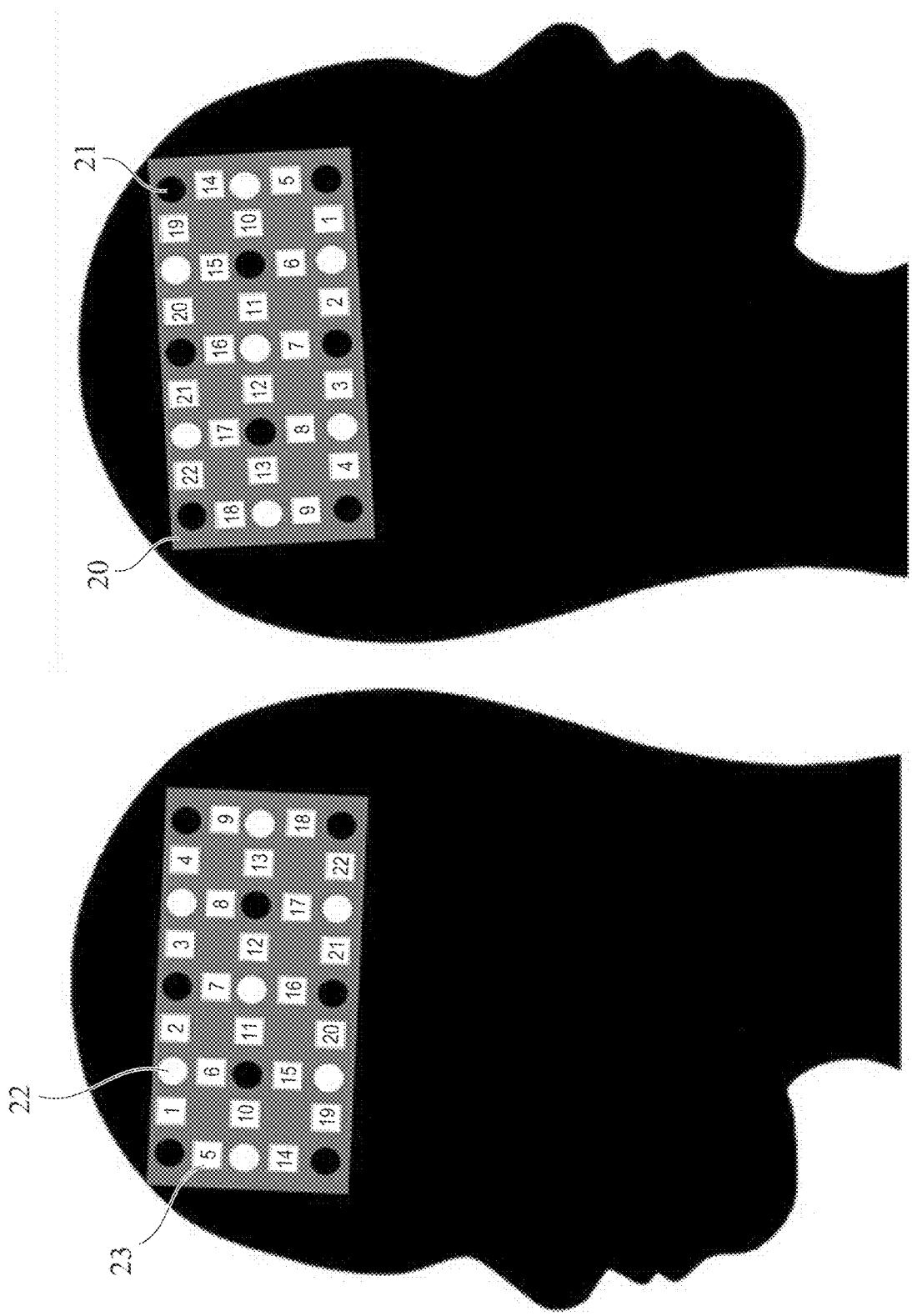
FIG. 2 is a diagram showing an exemplary arrangement of a measurement probe 20 attached to the head of a subject (a patient or healthy subject) for measuring biological signals (brain waves) of the patient.

FIG. 2 is a diagram showing an exemplary arrangement of a measurement probe 20 attached to the head of a subject (a patient or healthy subject) for measuring biological signals (brain waves) of the patient.

The measurement probe 20 includes a plurality of light sources 21, a plurality of detectors 22, and a plurality of measurement point channels 23. The arrangement of the measurement probe 20 is determined on the basis of the hypothesis of a predetermined task that the subject has executed. For example, in the case of a task of working memory, the measurement probe 20 is arranged in a portion of the prefrontal area.

<Configuration of GUI>

Figure 3:
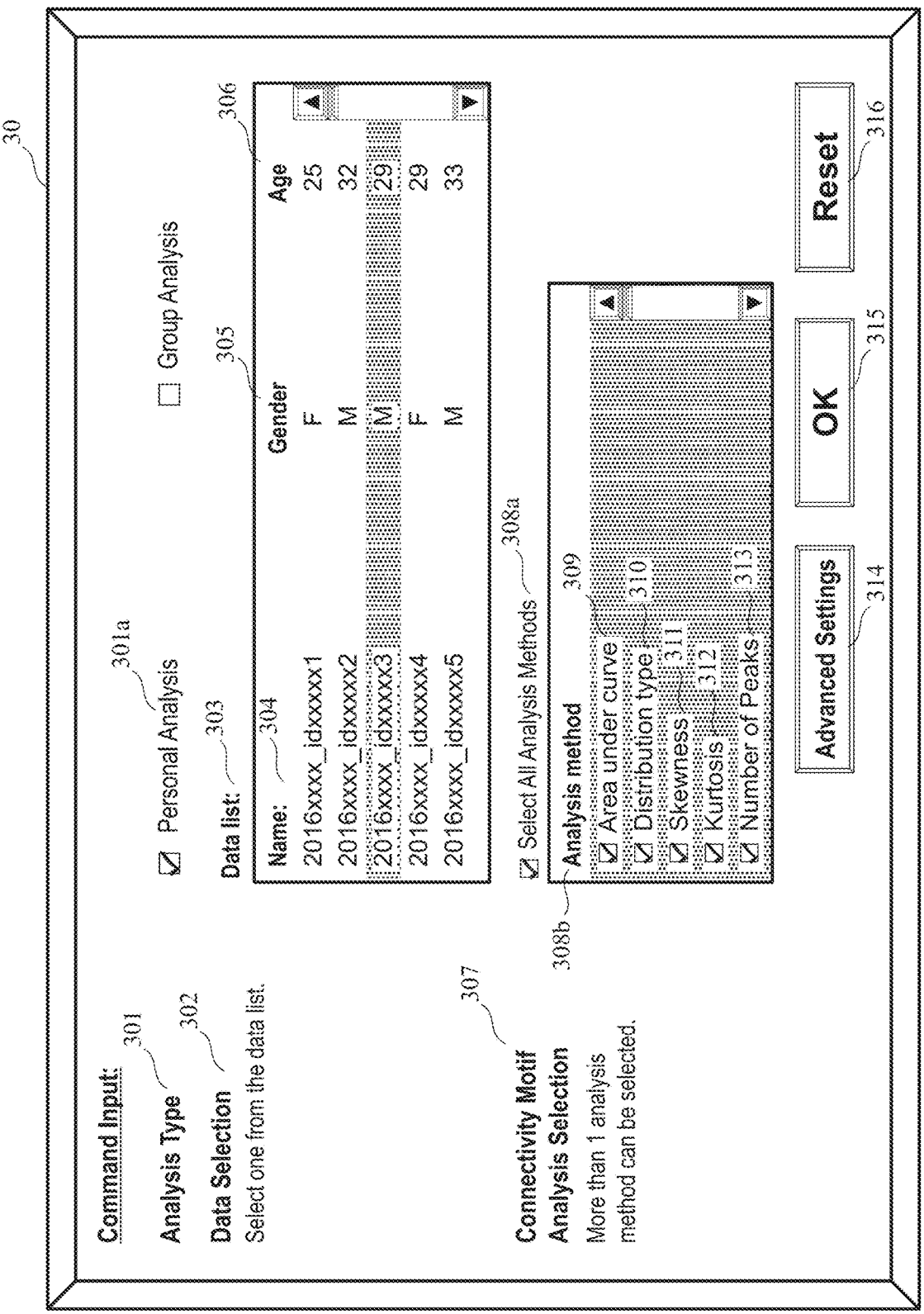
FIG. 3 is a diagram showing a command input screen 30 when an operator selects personal analysis 301a as an analysis type 301.
Figure 5:
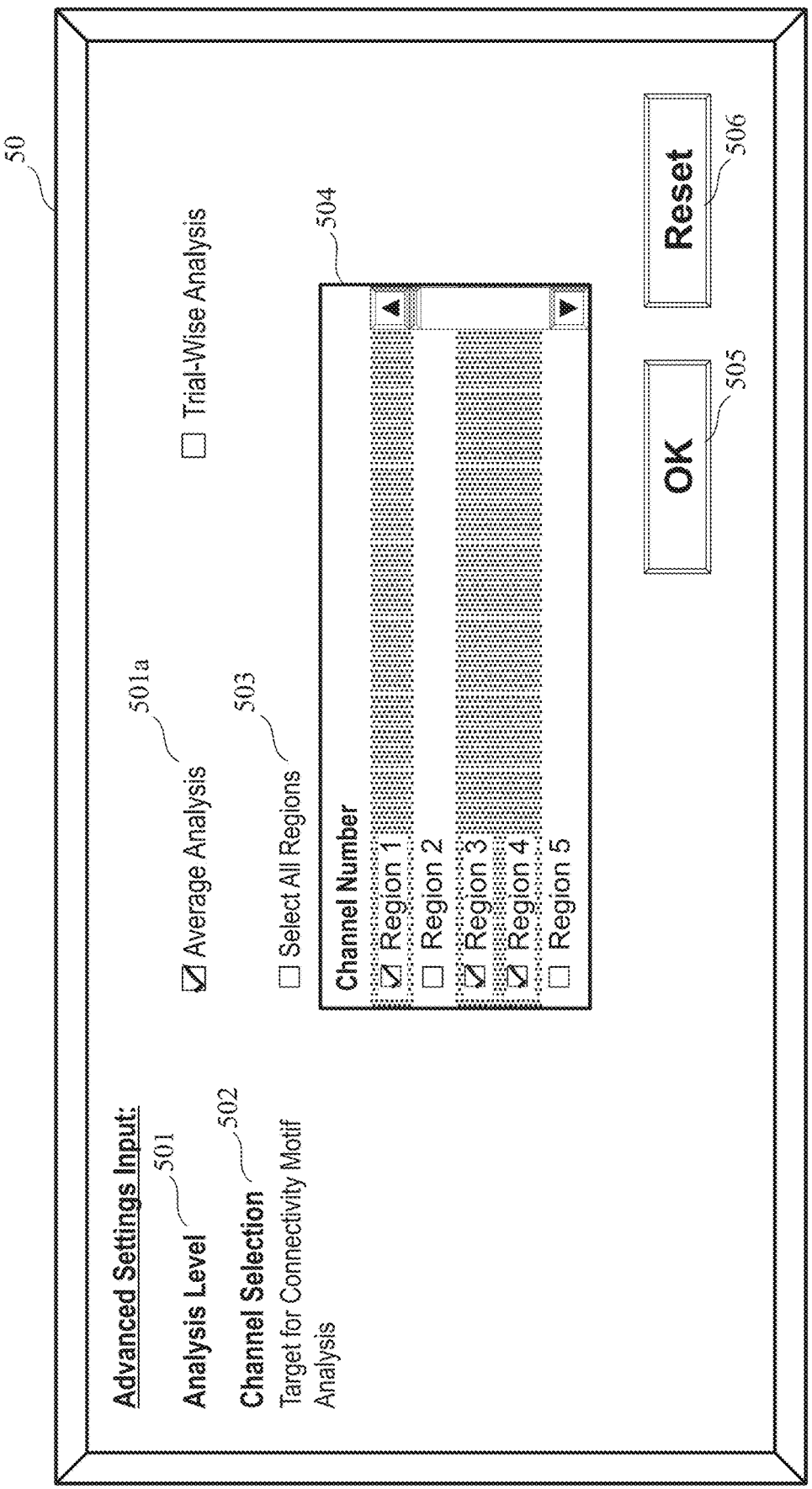
FIG. 5 is a diagram showing a command input screen 50 when an operator selects average analysis as advanced settings 314 on the command input screen of FIG. 3 or FIG. 4.
Figure 6:
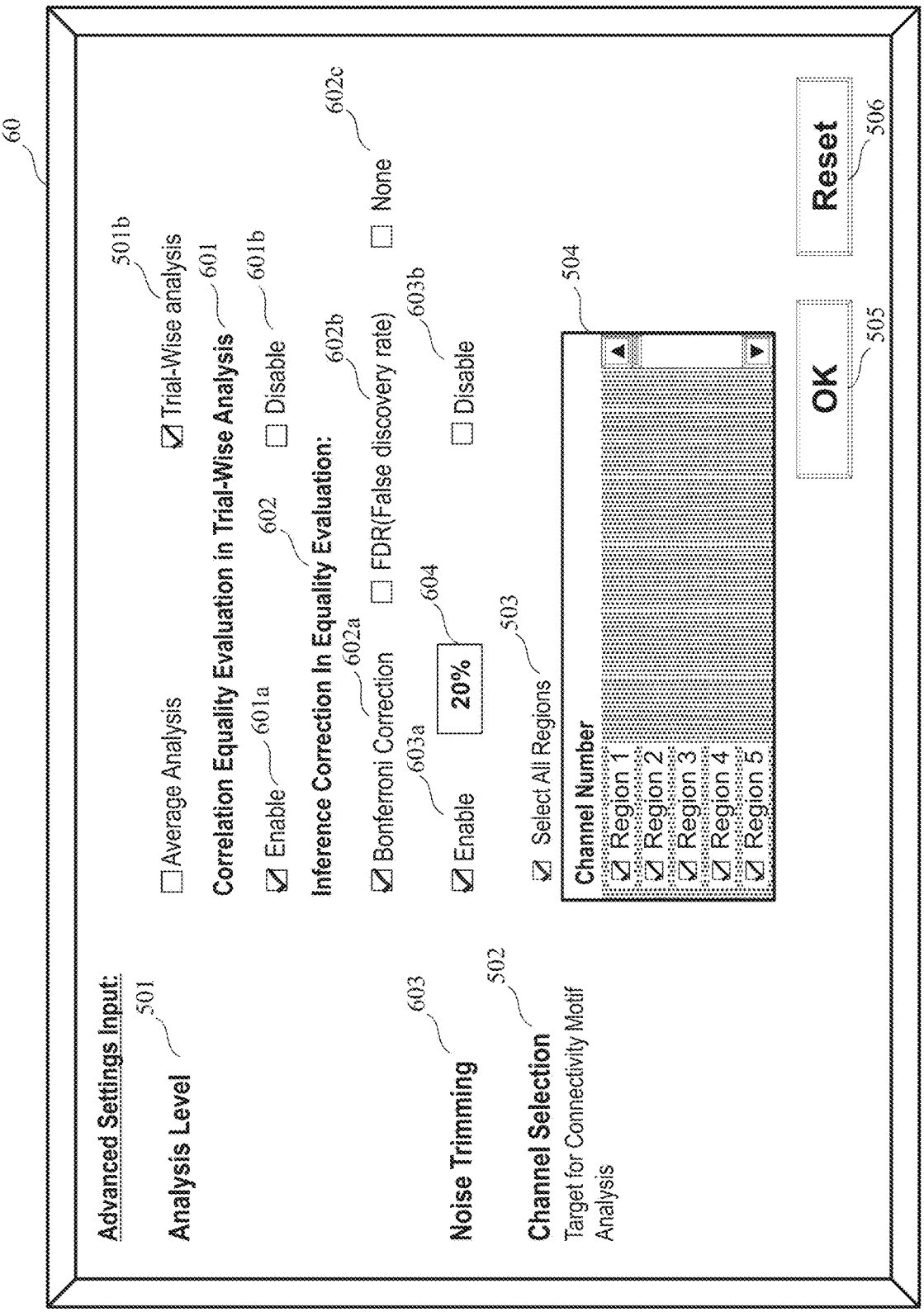
FIG. 6 is a diagram showing a command input screen 60 when an operator selects trial (also referred to as examination)-wise analysis as the advanced settings 314 on the command input screen of FIG. 3 or FIG. 4.

FIGS. 3 to 6 are diagrams each showing an exemplary configuration of a GUI for an operator to input a command. FIG. 3 is a diagram showing a command input screen 30 when an operator selects personal analysis 301a as an analysis type 301. FIG. 4 is a diagram showing a command input screen 40 when an operator selects group analysis 301b as the analysis type 301. FIG. 5 is a diagram showing a command input screen 50 when an operator selects average analysis 501a as advanced settings 314 on the command input screen of FIG. 3 or FIG. 4. FIG. 6 is a diagram showing a command input screen 60 when an operator selects trial (also referred to as experiment)-wise analysis 501b as the advanced settings 314 on the command input screen of FIG. 3 or FIG. 4.

If the personal analysis 301a is selected, as shown in FIG. 3, the brain connectivity analysis system 1 (in the following description, the "processor 11" will be described as a subject that performs each operation because the processor 11 executes each program) displays data selection (a data selection field) 302 including a data list 303 on the command input screen 30 so that personal (subject's) data can be selected. In the data list 303, data on a plurality of subjects registered in the personal database 141 is displayed. Data on each subject includes at least the name, anonymity, or ID number (hereinafter referred to as name) 304, the gender 305 of the subject, and the age 306 of the subject. An operator is requested to select data on a single subject from among the data on the plurality of subjects. In addition, the processor also displays connectivity motif analysis selection (a connectivity motif selection field) 307 for designating an analysis method on the command input screen 30. The connectivity motif analysis selection 307 includes an all-analysis-method selection portion 308a and an individual-analysis-method selection portion 308b. Herein, as the analysis methods, analyses of the area under the distribution curve (area under curve), distribution type, skewness, kurtosis, and the number of peaks are prepared in advance, for example. However, the analysis methods are not limited thereto and other analysis methods may also be included. When data on a subject and an analysis method are selected and the operator clicks an OK button 315, selection of the data and the analysis method is completed. Meanwhile, when the operator clicks a Reset button 316, the input command is reset. When selection of data on the subject and the analysis method is OK, the screen switches to a screen for advanced settings input (see FIGS. 5 and 6).

If the group analysis 301b is selected, as shown in FIG. 4, the processor 11 displays the data selection (the data selection field) 302 including a data list of a group 1_401 and a data list of a group 2_402 on the command input screen 40 so as to allow for comparison between at least data on a person (a subject) as a comparison source and a person (a subject) as a comparison target. Each of the data lists of the group 1_401 and the group 2_402 displays data on a plurality of subjects registered in the personal database 141. The data on each subject includes at least the name 404, the gender 405 of the subject, and the age 406 of the subject. An operator is requested to select at least data on a single subject from each group. If comparison between a single subject and another group (for example, a population) is to be performed, the operator selects data on a single subject from the data list 401 of the group 1, and also selects data on some or all of the subjects, which exclude data on the subject selected from the group 1, from the data list of the group 2_402. In addition, the processor displays the connectivity motif analysis selection 307 for designating an analysis method on the command input screen 40. The connectivity motif analysis selection 307 includes the all-analysis-method selection portion 308a and the individual-analysis-method selection portion 308b. Herein, as the analysis methods, the area under the distribution curve (area under curve) and the like are prepared in advance, for example. However, the analysis methods are not limited thereto and other analysis methods may also be included. When data on a subject and an analysis method are selected and the operator clicks the OK button 315, selection of the data and the analysis method is completed. Meanwhile, when the operator clicks the Reset button 316, the input command is reset. When selection of data on the subject and the analysis method is OK, the screen switches to a screen for advanced settings input (see FIGS. 5 and 6).

In the advanced settings input, if the operator selects the average analysis 501a, the command input screen 50 is displayed, and if the trial-wise analysis 501b is selected, the command input screen 60 is displayed.

If the average analysis 501a is selected, as shown in FIG. 5, the processor 11 displays channel selection 502 on the command input screen 50 for designating on which channel(s) connectivity motif analysis is to be performed. The channel selection 502 includes an all-region selection portion 503 to place check marks when all of the prepared channels (regions) are to be selected, and an individual-region selection portion 504 to place check marks when two or more of the channels (regions) are to be individually selected. When the analysis level and a target channel(s) to be analyzed are selected and the operator clicks an OK button 505, input of all commands is completed. Meanwhile, when the operator clicks a Reset button 506, the selection of the analysis level and the target channel is reset.

If the trial-wise analysis 501b is selected, as shown in FIG. 6, the processor 11 displays a selection portion for selecting whether to enable correlation equality evaluation (a correlation equality evaluation selection portion for trial-wise analysis) 601, and an inference correction selection portion 602 for equality evaluation. In the correlation equality evaluation selection portion 601 for trial-wise analysis, if a check mark is placed in the enable 601a, correlation equality evaluation is executed. If a check mark is placed in the disable 601b, correlation equality evaluation is not executed. In the inference correction selection portion 602 for equality evaluation, Bonferroni correction 602a, FDR (false discovery rate) 602b, and none 602c are selectable. If the Bonferroni correction 602a is selected, Bonferroni correction is applied to the correlation equality evaluation results of the trial-wise analysis. If the FDR 602b is selected, FDR is calculated for the correlation equality evaluation results of the trial-wise analysis. If the none 602c is selected, the correlation equality evaluation results of the trial-wise analysis are directly output. In addition, the processor 11 displays a noise trimming selection portion 603 for selecting whether to execute noise trimming (noise elimination). In the noise trimming selection portion 603, if a check mark is placed in the enable 603a, a noise trimming process is executed. In such a case, the operator is prompted to input the maximum percentage 604 of trimming. If a check mark is placed in the disable 603b, a noise trimming process is not executed and the results are presented as they are. Further, the processor 11 displays the channel selection 502 for selecting a target channel(s) to be analyzed. The channel selection 502 includes the all-region selection portion 503 for placing check marks when all of the prepared channels (regions) are to be selected, and the individual-region selection portion 504 for placing check marks when two or more of the channels (regions) are to be individually selected. If the selectable channels (regions) are limited, a default parameter for analyzing a connectivity motif is used. When the analysis level, whether to perform noise trimming, and a target channel(s) to be analyzed are selected and the operator clicks the OK button 505, input of all commands is completed. Meanwhile, when the operator clicks the Reset button 506, the selection of the analysis level, whether to perform noise trimming, and the target channel(s) to be analyzed is reset.

As described above, the display configuration of the command input screen dynamically changes depending on the types of commands input by the operator as shown in the command input screens 30 to 60.

<Brain Connectivity Analysis Process>

Figure 7:
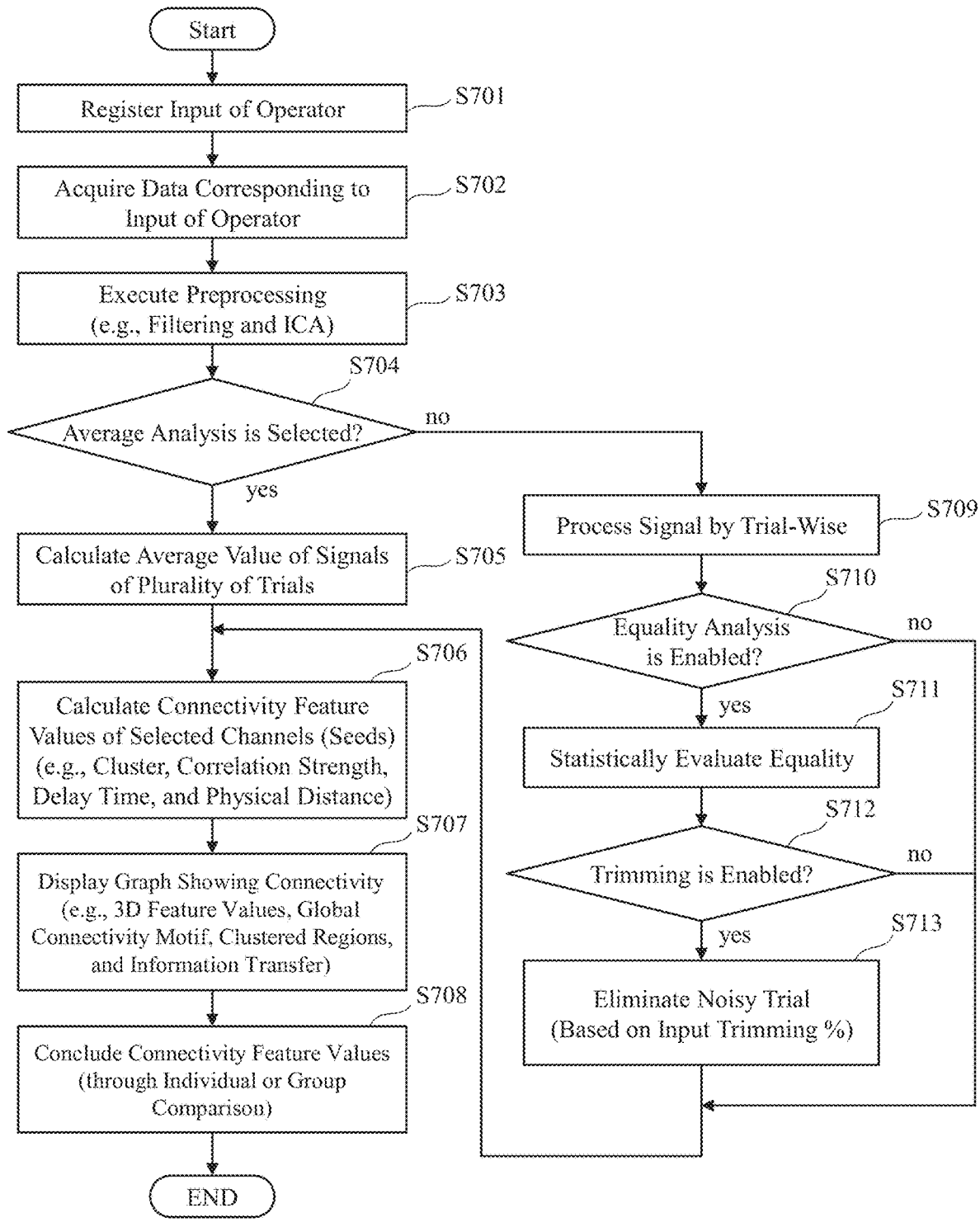
FIG. 7 is a flowchart illustrating a brain connectivity analysis process executed by the brain connectivity analysis system 1.

FIG. 7 is a flowchart illustrating a brain connectivity analysis process executed by the brain connectivity analysis system 1. The process shown in the flowchart of FIG. 7 corresponds to the process in each step of the comprehensive connectivity analysis program 122. However, since the comprehensive connectivity analysis program 122 is executed by the processor 11, each process will be described as being performed by the processor 11 in the following.

(i) Step 701

When an operator has input commands in accordance with the command input screens 30 to 60, the processor 11 registers the commands in the memory 16 as the input of the operator. The input (command) of the operator registered in the memory 16 is read from the memory 16 in each of the following steps as appropriate, and is used to execute a process in each step.

(ii) Step 702

The processor 11 acquires from the personal database 141 and the measurement database 142 data on a subject corresponding to the items designated in the data selection 302 and the channel selection 502 (which includes measured data on each of the selected channels) among the commands input by the operator.

(iii) Step 703

The processor 11 executes preprocessing on the measured data on the subject (individual and/or group) acquired in step 702. Examples of preprocessing include a filtering process and independent component analysis (ICA).

(iv) Step 704

The processor 11 checks the input of the operator registered in the memory 16, and determines if the average analysis 501a is selected as the analysis level 501. If the average analysis 501a is selected (if Yes in step 704), the process proceeds to step 705. If the average analysis 501a is not selected, that is, if the trial-wise analysis 501b is selected (if No in step 704), the process proceeds to step 709.

(v) Step 705

The processor 11 calculates, for the acquired measured data on the subject, the average value of signals of a plurality of trials for each of the selected channels included in the input command. For example, if the region 5 and the region 6 are designated as the target channels to be analyzed, the measured signals of the region 5 and the region 6 are each averaged.

(vi) Step 706

The processor 11 calculates connectivity feature values for each channel (region) selected by the operator as a seed. Each channel can become either a seed or a target in an analysis process. In comprehensive connectivity analysis, a seed changes during the analysis process. It should be noted that the operator may also designate a specific channel as a seed. In such a case, connectivity analysis is performed on the designated channel as a seed and on other channels as targets.

Connectivity feature values are calculated through, for example, network theories (small world analysis) including clustering and modularity (relationship between clusters); functional relationship analysis such as calculation of the correlation strength between channels; causal analysis including calculation of the transfer direction and transfer delay time in information transfer between channels; and the actual physical distance between channels (e.g., linear or approximate brain perimeter distance).

(vii) Step 707

The processor 11 generates a corresponding graph on the basis of the connectivity feature values calculated in step 706, and displays it on the display screen of the output unit (display device) 15. Examples of the displayed graph include a clustering map (see FIG. 11), a connectivity feature graph (see FIG. 13), and a global connectivity motif (see FIG. 14.). At least one of such graphs is generated and drawn. It should be noted that such connectivity feature values are concluded in accordance with the pre-set analysis type (personal analysis 301a or group analysis 301b) using the global connectivity motif (see FIG. 14).

(viii) Step 708

If individual comparison, individual-group comparison, or group comparison is designated by an input command of the operator, the processor 11 displays graphs of connectivity feature values calculated on the basis of the measured data on the individuals or groups on the display screen (for example, in parallel) so that the graphs can be compared. Through such comparison display, it becomes possible to classify the subjects into healthy, disorder-diagnosed, particular-stage disorder, and medicated subjects, for example.

(ix) Step 709

If the trial-wise analysis 501b is selected (No in step 704), the processor 11 extracts measured data on each trial from the data acquired in step 702.

In the trial-wise analysis, measured data on each trial is processed equally with the same time frame. Therefore, such analysis that uses measured data on each trial is superior to the aforementioned average analysis.

During Measurement, noise may appear randomly in the measured data on each trial. Although such noise is desirably eliminated, it is sometimes difficult to distinguish between noise and genuine biological data in the measured data. Meanwhile, if averaged data (which is used in average analysis) is used, the risk of noise at a particular time may be overlooked. If there are noises that affect the trial data, the resulting noise-affected trial data may not be equal to other trial data, and in such a case, the noise-affected trial data can be figured out. Because of such a benefit, the trial-wise analysis is supplemented by an option to select whether to perform a noise elimination process by the operator.

(x) Step 710

The processor 11 determines if the equality analysis (in FIG. 6, correlation equality evaluation in trial-wise analysis) is enabled by a command input by the operator. If the equality analysis is enabled (Yes in step 710), the process proceeds to step 711. If the equality analysis is disabled (No in step 710), the process proceeds to step 706.

When the process proceeds to step 706, the processor calculates connectivity feature values using measured data on each trial for each channel as a seed (measured data on all trials not subjected to equality analysis or trimming process). For example, in correlation analysis, if the number of trials for each channel is k (k=1, 2, . . . , n), a correlation value between the measured data on the seed channel (region) and the target channel for the k-th trial is calculated.

(xi) Step 711

If the equality analysis is enabled, the processor 11 executes equality analysis of the measured data on each trial to statistically evaluate the equality. From the statistical results of the equality analysis, data on the most noisy trail and the least noisy trail are temporarily stored in the memory 16 or the storage unit 14.

(xii) Step 712

The processor 11 determines if the trimming process is enabled by a command input by the operator. If the trimming process is enabled, the processor 11 further checks the maximum percentage 604 of the trimming process indicating the percentage of trial data to be eliminated.

If the trimming process is enabled (if Yes in step 712), the process proceeds to step 713. If the trimming process is disabled (if No in step 712), the process proceeds to step 706.

In such a case, connectivity feature values are calculated for measured data on each trial that has been subjected to equality analysis but has not been subjected to a trimming process.

(xiii) Step 713

The processor sequentially eliminates noisy trial data from data on the plurality of trials in order of decreasing noise level on the basis of the maximum percentage 604 of the trimming process included in the input command of the operator so that the eliminated data does not exceed the maximum percentage 604.

When measured data on noisy trials are eliminated, the process proceeds to step 706 so that connectivity feature analysis is performed on the measured data from which the measured data on the noisy trials have been eliminated.

Unlike the average analysis, the trial-wise analysis analyzes the connectivity features for measured data on each trial for a given channel (region) with respect to measured data on each trial for other channels (regions). In the trial-wise analysis, measured data of a particular trial order is associated with measured data of the same trial order. After the connectivity feature values for each trial are calculated, such connectivity feature values are averaged for all trials (excluding trimmed trials) and are visualized on connectivity graphs (step 707).

<Specific Example of Average Analysis (Matrix Correlation Results)>

Figure 8:
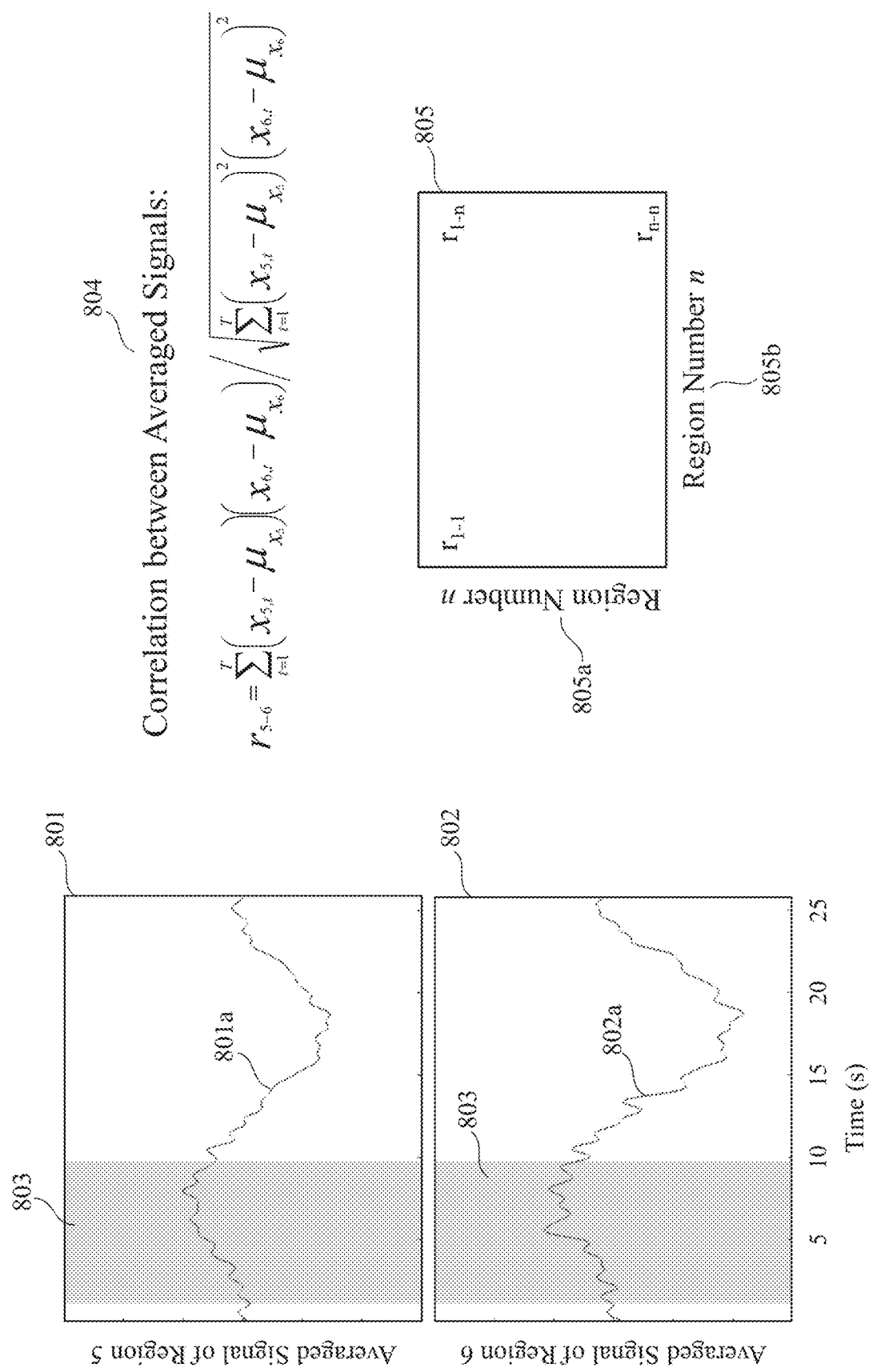
FIG. 8 is a diagram illustrating an example of an average analysis executed by the brain connectivity analysis system 1 in accordance with an embodiment.

FIG. 8 is a diagram illustrating an example of an average analysis process executed by the brain connectivity analysis system 1 in accordance with this embodiment.

In the average analysis process, for example, the correlation between an averaged signal 801a of a plurality of trials from a channel (region) 5_801 and an averaged signal 802a of a plurality of trials from a channel (region) 6_802 is analyzed. The trial period 803 corresponds to the time period of the region 5_801 and the region 6_802.

In the average analysis, when the correlation between two regions (in FIG. 8, the channel (region) 5 and the channel (region) 6) is computed, the cross-correlation between averaged signals of the two regions is computed in accordance with Equation 804. Equation 804 is an equation for determining the Pearson's correlation coefficient, where t indicates the sampling time, x indicates the amplitude value of a signal from each region at the sampling time t, and μ indicates the average value of signals within the trial period 803 for each region. Such a correlation coefficient determination process is also executed on other channels (regions).

The correlation coefficients calculated for the respective regions (channels) are stored in a 2D array 805 indicating the channel-channel (region-region) relationship. In the 2D array 805, the x-axis (805) and the y-axis 805b each indicate the region number n.

The computation performed in the average analysis is simpler as compared to that in the trial-wise analysis described below (see FIG. 9), and is convenient for comprehensively understanding the tendency of the correlation between regions.

<Specific Example of Trial-Wise Analysis (Matrix Correlation Results)>

Figure 9:
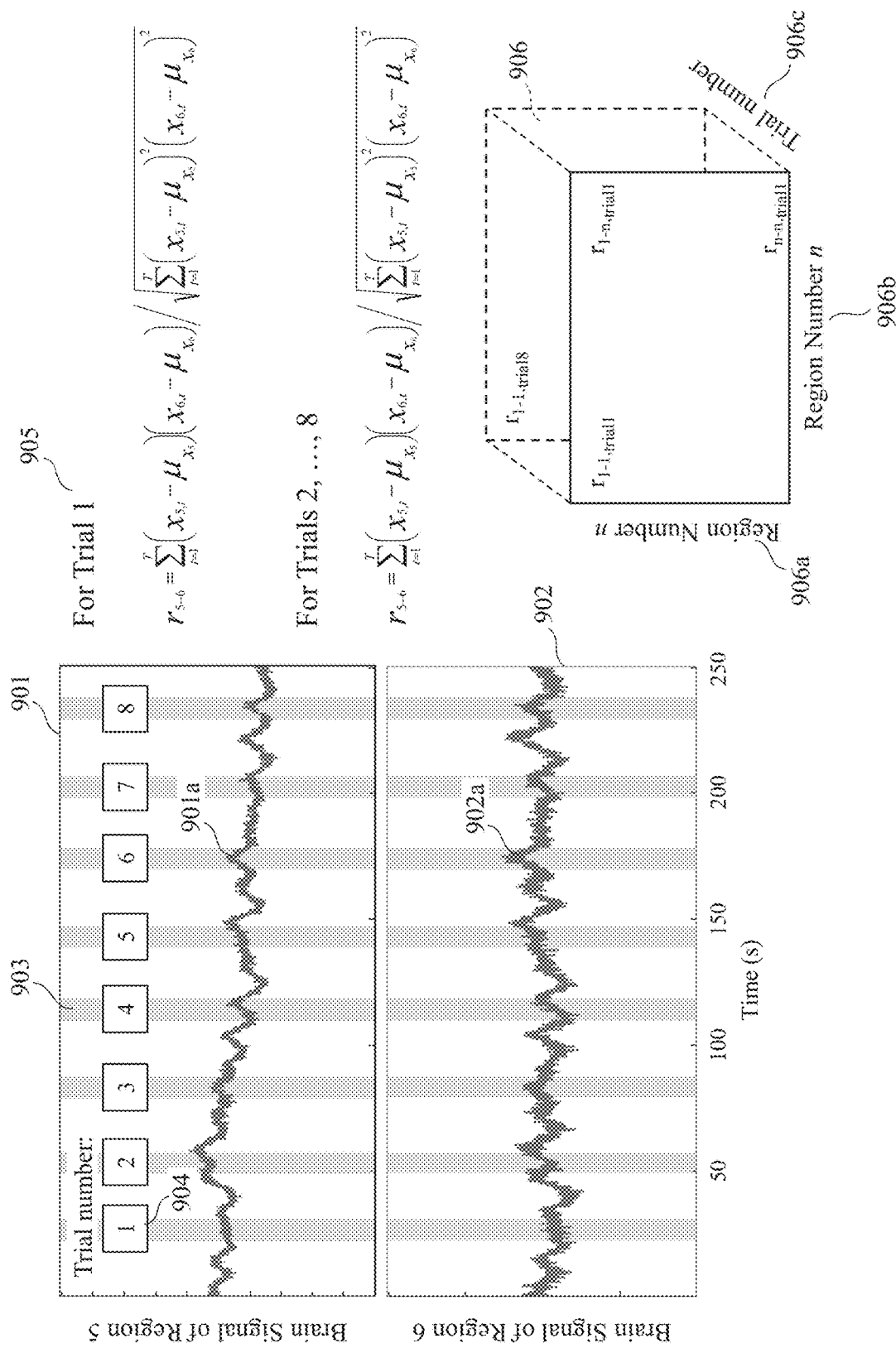
FIG. 9 is a diagram illustrating an example of a trial-wise analysis process executed by the brain connectivity analysis system 1 in accordance with an embodiment.

FIG. 9 is a diagram illustrating an example of a trial-wise analysis process executed by the brain connectivity analysis system 1 in accordance with this embodiment.

In a trial-wise analysis process, for example, the correlation between continuous data (brain signal graph) 901 from the channel (region) 5 and continuous data (brain signal graph) 902 from the channel (region) 6 is analyzed. From the two brain signal graphs 901 and 902, several information such as a trial period and number are extracted. Information on the trial period is indicated by a time period 903. Herein, eight trials are conducted in one time measurement as represented by the trial number index 904.

To execute correlation analysis based on the trial-wise method, for example, the correlation between a signal of the trial 1 from the channel (region) 5 and a signal of the trial 1 from the channel (region) 6 is computed in accordance with Equation 905. Equation 905 is an equation for determining the Pearson's correlation coefficient, where t indicates the sampling time, x indicates the amplitude value of a signal from each region at the sampling time t, and μ indicates the average value of signals within the trial period 903 for each region. In a similar manner, the correlation between a signal of the trial 2 from the channel (region) 5 and a signal of the trial 2 from the channel (region) 6 is computed. Such a correlation coefficient determination process is also executed on other channels (regions).

The correlation coefficient computed for each trial and region is stored in a 3D array 906 indicating the channel-channel (region-region) relationship for each trial between channels (regions). In the 3D array 906, the x-axis 906a and the y-axis 906b each indicate the region number n from which the region-region relationship can be confirmed. In addition, the z-axis 906c indicates the trial number from which the trial-trial correlation can be confirmed.

Trial-wise analysis is a little more complex as compared to the average analysis. However, the risk of noise occurrence is not overlooked, and analysis of brain signals is thus possible.

<Specific Example of Trimming Process>

Figure 10:
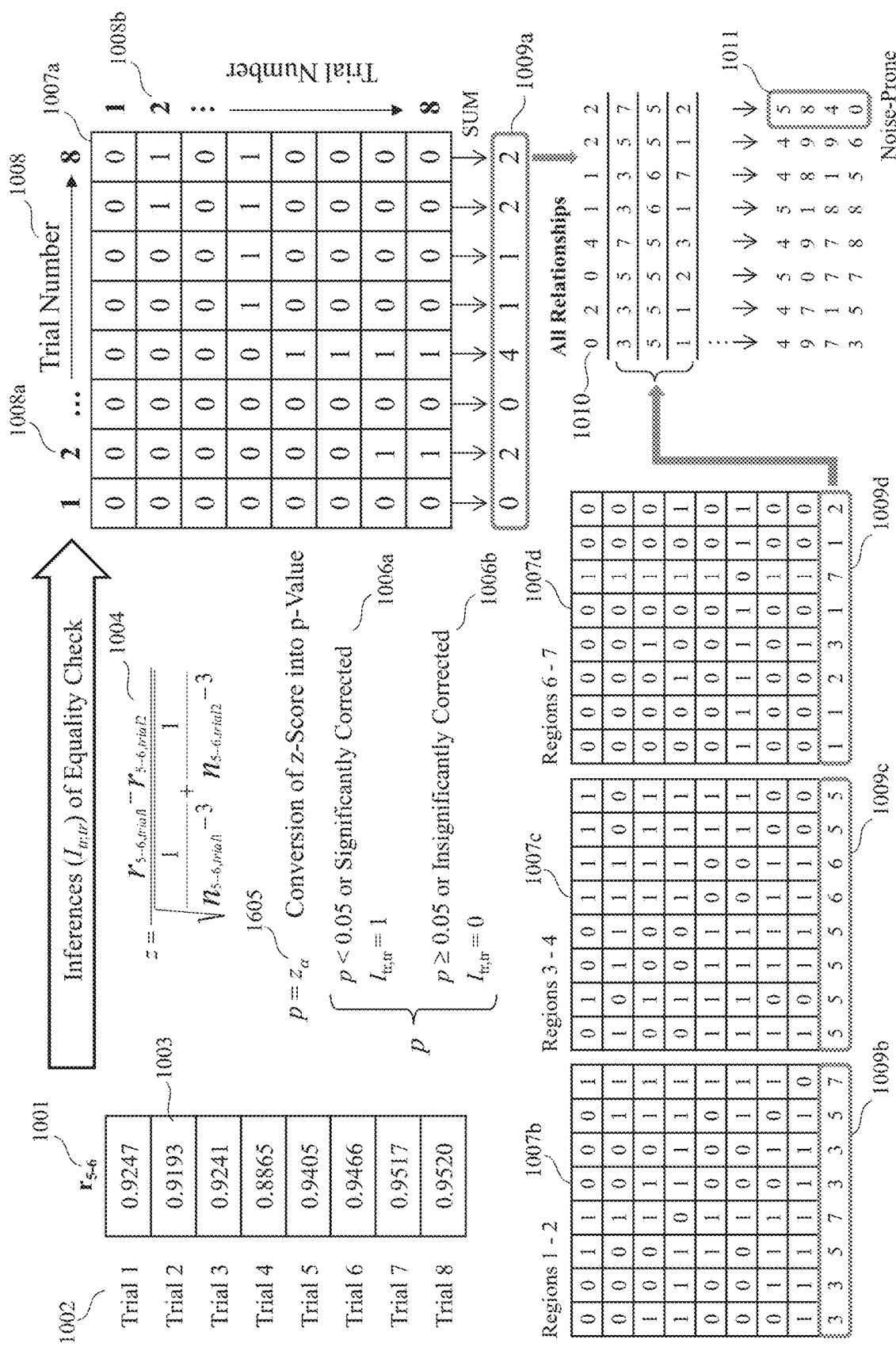
FIG. 10 is a diagram illustrating a specific example of a trimming process (noise elimination process) executed using information on the trial-trial correlation.

FIG. 10 is a diagram illustrating a specific example of a trimming process (noise elimination process) executed using information on the trial-trial correlation.

In FIG. 10, a table 1001 shows the correlation between the channel (region) 5 and the channel (region) 6. In the table 1001, each row of reference numeral 1002 indicates the trial number, and reference numeral 1003 indicates the trial-wise correlation coefficient. To detect noisy trials, the equality for a trial to other trials should be evaluated using Equation 1004 for determining the z-score. In Equation 1004, r indicates the correlation coefficient for each trial, and n indicates the data number within the trial period or the sampling number. Equality evaluation can be performed by calculating the z-score for all combinations of trials, for example, a combination of the trial 1 with other trials, a combination of the trial 2 with other trials, and a combination of the trial 3 with other trials. The z-score obtained from Equation 1004 is converted into the p-value in accordance with the z-distribution as indicated by Equation 1005.

The p-value ranges from 0 to 1 and is an index indicating the probability that a value greater than the test statistic value may be obtained under the condition that the null hypothesis $H_0$ is correct. In the specific example, the p-value is compared with a threshold with an independence level (set to 0.05 by default). If the p-value is less than 0.05, the null hypothesis $H_0$ is rejected, and "1" is assigned as the independence level index $I_{tr,tr}$ (1006a). The independence level index of "1" indicates that two correlation coefficients from two trials are unequal or one of two trials may be affected by noises. Otherwise, if the p-value is greater than or equal to 0.05, "0" is assigned as the independence level index $I_{tr,tr}$ (1006b). The independence level index "0" indicates that two correlation coefficients from two trials are equal or two trials are noise-free.

Such independence level indices "0" and "1" are arranged in an evaluation array 1007a of the channels (regions) 5 and 6. In the evaluation array 1007a, trial numbers are arranged in the x-axis 1008a and the y-axis 1008b, and combinations of trials 1 to 8 are arranged. That is, in the specific example, the independence level index of the trial 1 and the trial 1, the independence level index of the trial 1 and the trial 2, . . . , and the independence level index of the trial 8 and the trial 8 are arranged. Then, the independence level indices are summed vertically and the summation results 1009a are output. The summation results 1009a indicate the values of equality evaluation of trials for the channel (region) 5 and the channel (region) 6. These procedures are conducted for all of the other region-region (trail-trial) relationships to compute evaluation arrays 1007b to 1007d . . . of the independence level indices, and the summation results 1009b to 1009d . . . of the indices are determined. Further, the summation results for relationships other than the relationship of similar regions (e.g., channel (region) 1-1, channel (region) 2-2, . . . channel (region) 8-8) are arranged (see reference numeral 1010), and grand summation is vertically performed. From the result of grand summation, the higher sum indices (see reference numeral 1011) show more noise-prone or high inequality compared to other trials while the lower sum indices show less noise-prone trials or less inequality compared to other trials. Furthermore, this result also indicates the noise level for each trial and thus can sort the trials. From the specific example of FIG. 10, it is found that the trial 8 is likely to be the most noise-affected trial and the trial 2 is likely to be the least noise-affected trial.

If the command 603a enabling a trimming process is input by the operator, a trimming process (elimination of trial data) is executed in accordance with the percentage 604 input together with the command 603a. For example, as shown in FIG. 6, if 20% is designated as the percentage 604, 20% of trial data is sequentially eliminated starting from the more noise-prone trials of the 8 trials. Since 20% trial trimming from eight trials is 1.66 trials that is impossible, 1.66 is rounded down so that one trial data that is most noise-prone, that is, trial data with the trial number 8 is eliminated.

Since noise-prone trial data that may possibly adversely affect analysis is eliminated as described above, more accurate connectivity analysis is possible.

<Exemplary Configuration of Distribution Map of Clustering Coefficients>

Figure 11:
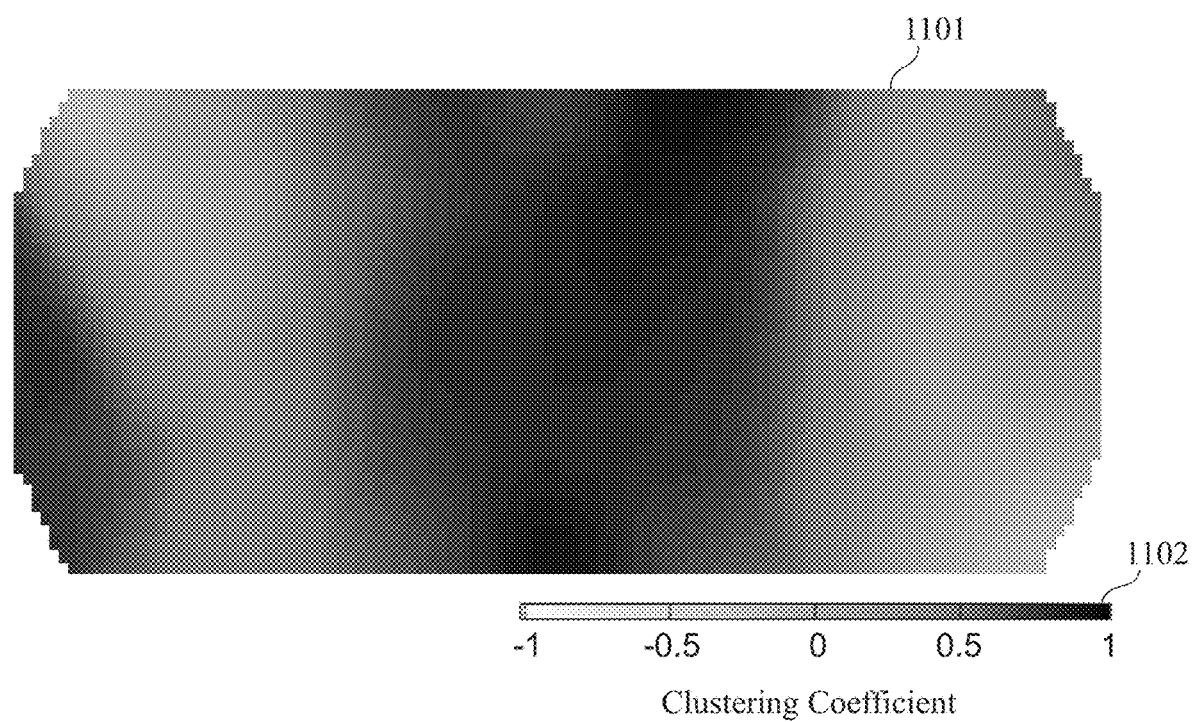
FIG. 11 is a diagram showing an exemplary configuration of a distribution map of clustering coefficients obtained from a measured channel (region)

FIG. 11 is a diagram showing an exemplary configuration of a distribution map of clustering coefficients obtained from a measured channel (region). FIG. 11 is a distribution map 1101 of clustering coefficients of the brain's prefrontal area.

To generate a distribution map, a clustering coefficient is calculated for each channel (region) by computing the correlation strength of the channel (region) with respect to the neighbor channels (regions) using Equation 1100.

$$C = \frac{\Sigma r}{n \times (n-1)} \qquad \text{Equation 1100}$$

Herein, C indicates the clustering coefficient from an analyzed channel (region), r indicates the correlation coefficients among direct neighbor channels (regions), and n indicates the number of direct neighbor channels (regions). The correlation coefficient r is the sum for bidirectional correlation, for example, the sum for the channel 2-3 relation and the channel 3-2 relation in the case of the channels 2 and 3.

To visualize the distribution map 1101, clustering coefficients of gaps between the channels (regions) are normally extrapolated. In the distribution map 1101, the clustering coefficient level 1102 is shown by a color map.

Displaying a distribution map of clustering coefficients as described above can visualize channels (regions) with higher clustering coefficients, and thus can identify channels (regions) that are associated with each other when a subject executes a given task.

<Display of Information Transfer Between Channels (Regions)>

Figure 12:
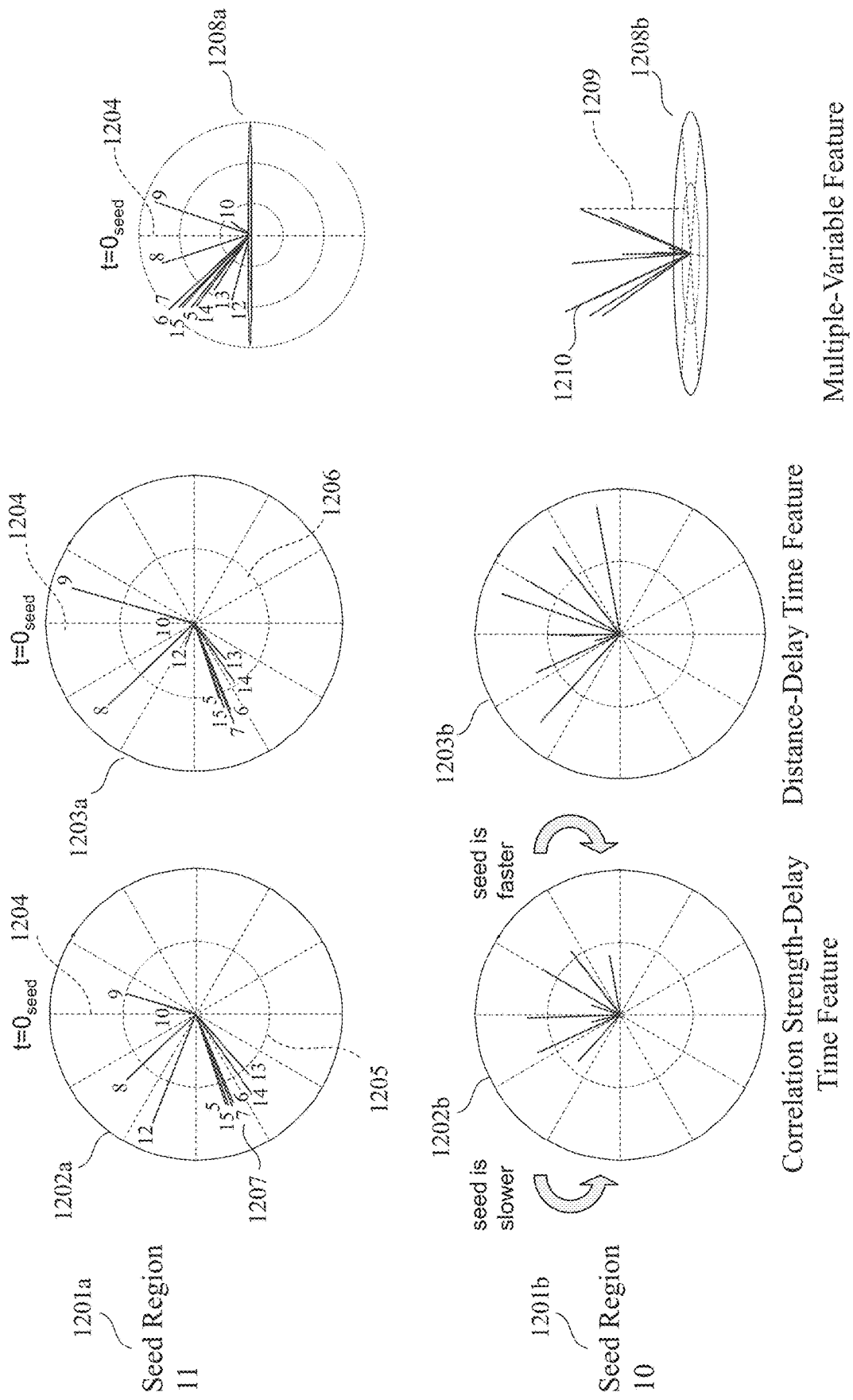
FIG. 12 is a diagram representing connectivity features when information is transferred from a given channel (seed) to other channels (targets)

FIG. 12 is a diagram representing connectivity features when information is transferred from a given channel (seed) to other channels (targets). In the following description, the processor 11 can be a subject that draws each diagram in FIG. 12.

When information is transferred from a given channel (seed channel) to another channel (target channel), a signal delivered to the target channel (target region) is expected to have a similar pattern to that of a signal of the seed channel (seed region). However, the signal pattern may slightly shift in the time direction due to a transfer delay time. Therefore, besides computation of the Pearson correlation coefficient, cross-correlation analysis is also executed to shift the signals step-by-step (according to sampling points), convolve signals, and determine the highest correlation and the amount of delay time as the signals are shifted. The cross-correlation equation is represented by Equation 1200.

$$c_{x_5 x_6}(k) = \begin{cases} \dfrac{1}{T} \sum_{t=1}^{T-k} (x_{5,t} - \overline{x_5})(x_{6,t+k} + \overline{x_6}); k = 0, 1, 2, \ldots \\ \dfrac{1}{T} \sum_{t=1}^{T-k} (x_{6,t} - \overline{x_6})(x_{5,t+k} + \overline{x_5}); k = 0, -1, -2, \ldots \end{cases}$$

Equation 1200

$$\sigma_{x_5} = \sqrt{c_{x_5 x_5}(0)}$$

$$\sigma_{x_6} = \sqrt{c_{x_6 x_6}(0)}$$

$$r_{x_5 x_6}(k) = \dfrac{c_{x_5 x_6}(k)}{\sigma_{x_5} \sigma_{x_6}}$$

Herein, x indicates the signal amplitude value at a particular sampling point of the channels (for example, channels 5 and 6), c indicates the covariance, T indicates the maximum trial period as with n, k indicates the shifted time, σ indicates the standard deviation of signals for each channel (region), and r indicates the correlation coefficient.

From the delay time, the direction of information transfer can be recognized. That is, a channel (region) in which a signal with a similar shape was measured the fastest is a seed channel, and thus, identifying the time when the signal with the similar shape was measured can identify a channel (region) as a transfer source channel to the target.

To draw the connectivity features including the correlation, delay time, information transfer direction, and the physical distance among channels (regions), 2D and 3D circle plots such as those shown in FIG. 12 can be used. To generate circle plots, a channel (region) is selected as a seed. In FIG. 12, an example is shown in which a channel (region) 11_1201*a* and a channel (region) 10_1201*b* are selected as seed channels (regions). To draw circle plots, the highest correlation strength and delay time when a signal from the seed channel (region) is cross-correlated to signals from other channels (regions) are acquired. In addition, the physical distance (linear coordinate or brain perimeter) between the seed channel (region) and other channels (regions) is also calculated. After such connectivity features are acquired, two circle plots 1202*a-b* and 1203*a-b* are drawn for the respective seed channels (regions). The circle plots 1202*a-b* for the respective seed channels (regions) represent the relationship between the correlation strength and time delay, and the circle plots 1203*a-b* for the respective seed channels (regions) represent the relationship between the physical distance and time delay.

Each line drawn by each circle plot in FIG. 12 represents the relationship between the seed channel (region) and other channels (regions). In addition, a vertical line 1204 on the circle plot indicates the zero time-delay. When a line is located at a position in the counter clock-wise direction from the vertical line 1204, it means that the signal from the seed channel (region) is slower than the correlated signals from other channels (regions) corresponding to the positions in the counter clock-wise direction from the vertical line 1204. Meanwhile, when a line is located at a position in the clock-wise direction from the vertical line 1204, it means that the signal from the seed channel (region) is faster than the correlated signals from other channels (regions) corresponding to the positions in the clock-wise direction from the vertical line 1204. Further, the distances (radii) from the centers of the circle plots as indicated by reference numerals 1205 and 1206 indicate the correlation strength and physical distance, respectively. The points nearer the center show the stronger correlation and closer physical distance. Lines from the centers of the circle plots show the correlation strength-delay time feature and the physical distance-delay time feature, respectively, between the seed channel (region) and other channels (regions).

For example, in the circle plot 1202*a* of the seed channel (region) 11, the signal from the seed channel (region) 11 is faster than the correlated signals from the channels (regions) 9 and 10, and thus, the seed channel (region) 11 can be estimated to be a source channel (region) of the channels (regions) 9 and 10. Further, the signal from the seed channel (region) 11 is slower than the correlated signals from the channels (regions) 5 to 8 and 12 to 15, and thus, the seed channel (region) 11 can be estimated to be a target channel (region) of the channels (regions) 5 to 8 and 12 to 15. While a 2D circle plot is represented by two axes of the radius and radiant, a 3D circle plot is augmented with another axis of the height. Herein, the radius 1210 represents the correlation strength, the angle represents the delay, and the height 1209 represents the physical distance.

Figure 15:
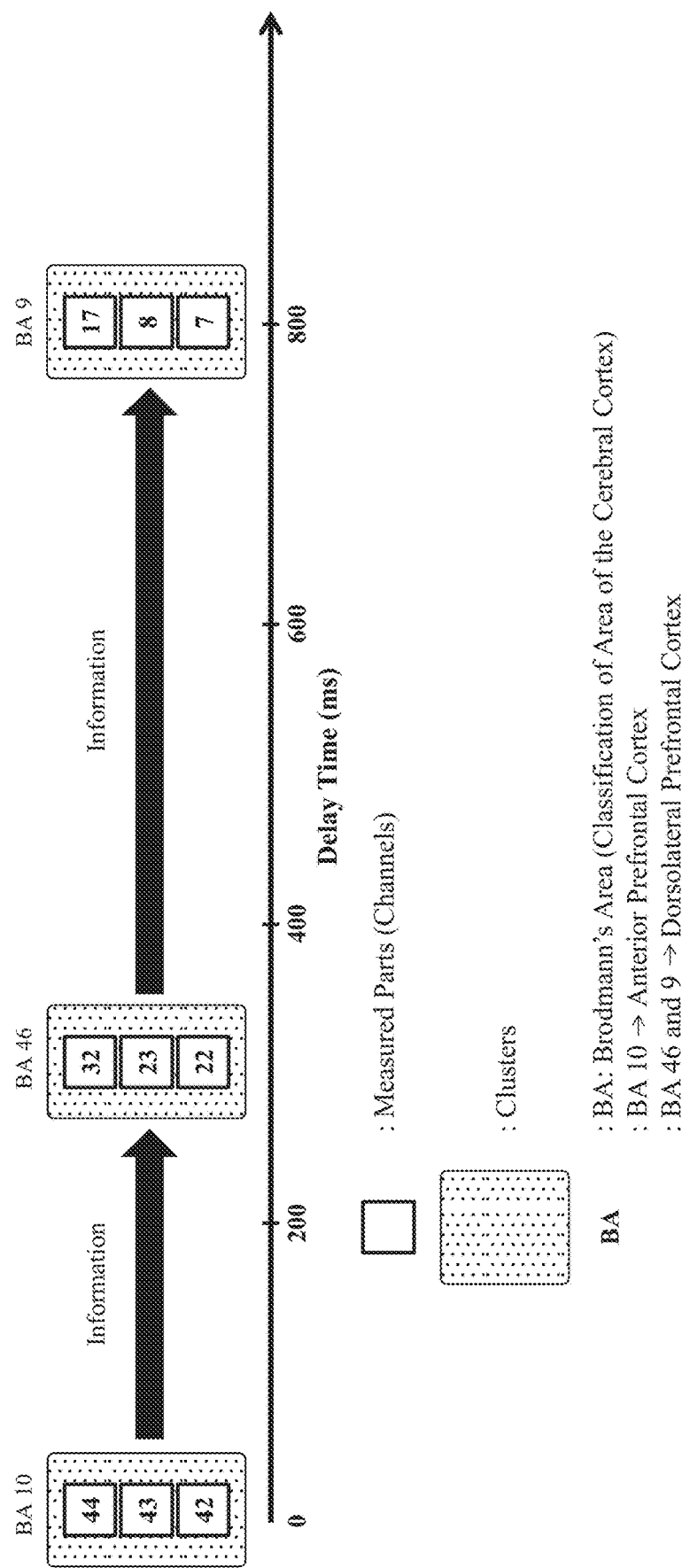
FIG. 15 is a diagram schematically showing information transfer between clusters formed by a plurality of channels (regions) and a delay time at that time.
Figure 16:
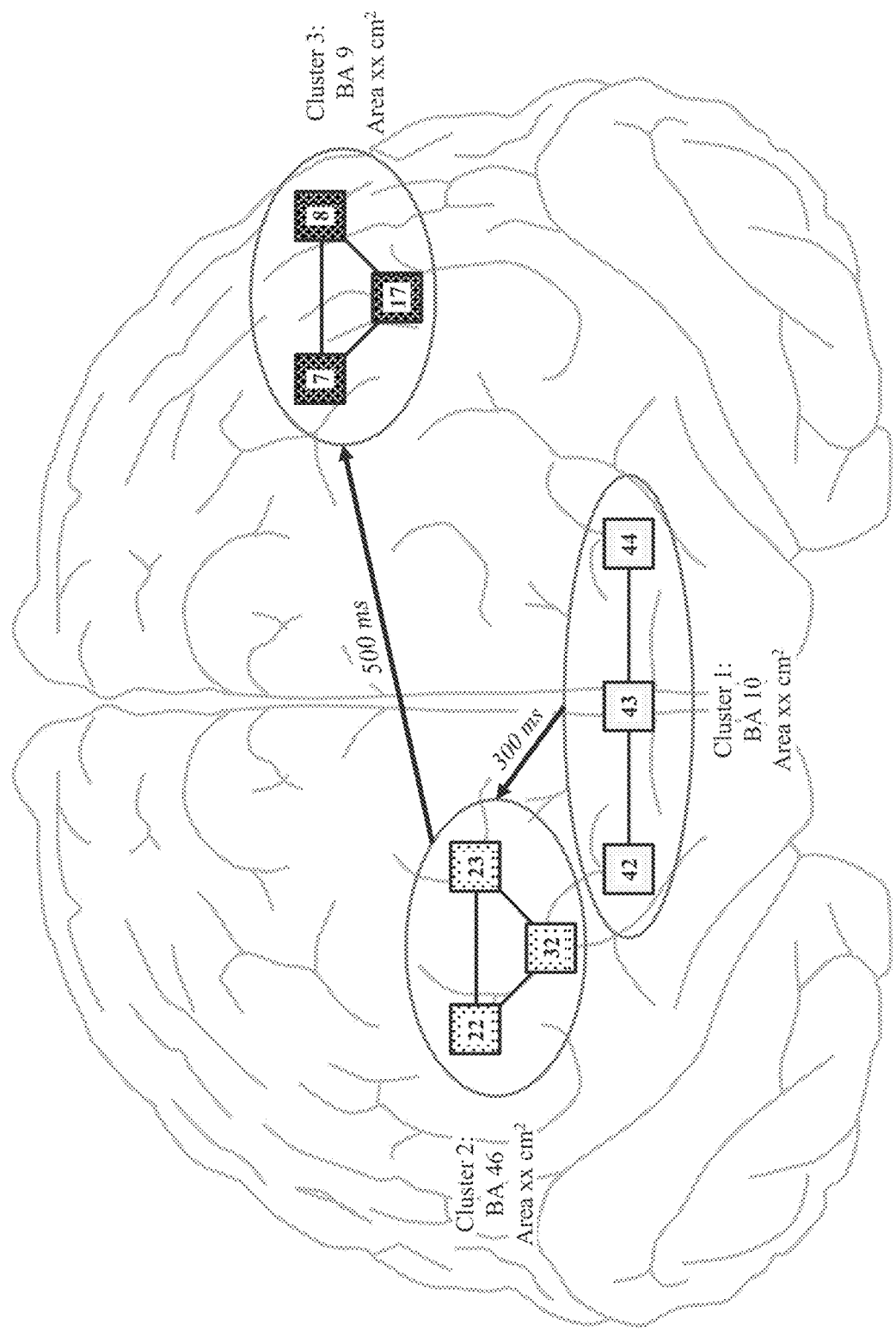
FIG. 16 is a diagram representing an example of the information transfer in FIG. 15 in association with brain regions.

FIG. 15 is a diagram schematically showing information transfer between clusters formed by a plurality of channels (regions) and a delay time at that time. As described above, a plurality of channels (regions) with high cross-correlation are grouped as clusters. When information is transferred, the process is performed on a cluster and the information is further transferred to the next cluster. The information transfer time herein appears as a delay time. FIG. 16 is a diagram representing an example of the information transfer in FIG. 15 in association with brain regions.

<Example of Group Comparison Regarding Global Connectivity>

Figure 13:
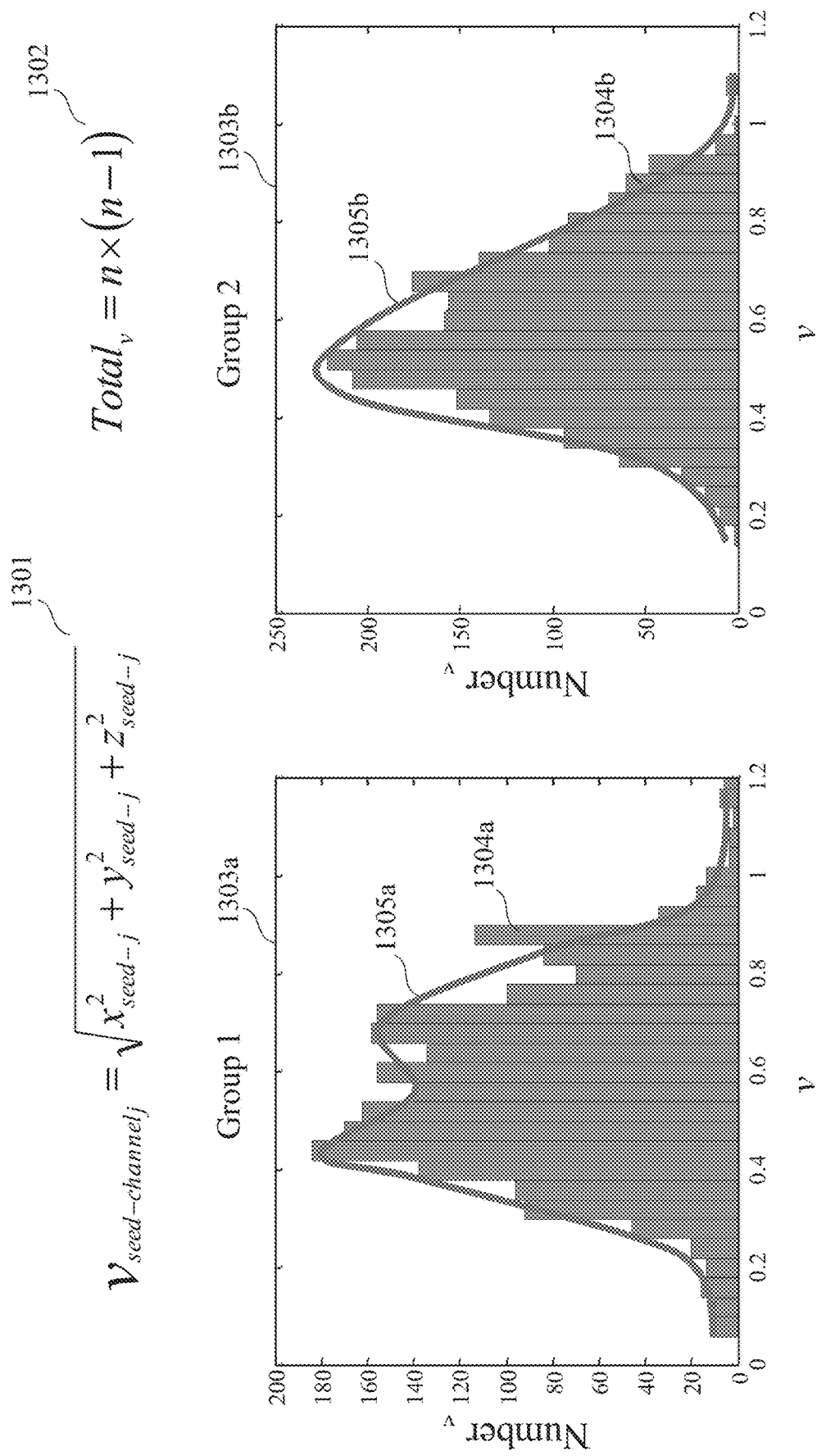
FIG. 13 is a diagram showing an exemplary data display for comparing global connectivity motifs between Groups 1 and 2 obtained by the brain connectivity analysis system 1 in accordance with an embodiment.

FIG. 13 is a diagram showing an exemplary data display for comparing global connectivity motifs between the groups 1 and 2 obtained by the brain connectivity analysis system 1 in accordance with this embodiment.

The brain connectivity analysis system 1 calculates connectivity features and draws the 3D circle plots 1208*a* to 1208*b* for n seed channels designated by the input command 605 of the operator as shown in FIGS. 12 and 13. Herein, n indicates the total number of the channels (regions) selected for the analysis. FIG. 13 shows an exemplary display in which the brain connectivity analysis system 1 performs a computation of integrating the connectivity of seed channels into global connectivity for increasing the robustness of analysis and minimizing the risk of misinterpretation in the analysis.

In FIG. 12, the 3D circle plots 1208*a* to 1208*b* each show the relationship (for example, cross-correlation) between a seed channel (region) and other channels (regions). However, in the computation of the brain connectivity analysis system 1 to integrate the connectivity of the seed channels into global connectivity, the central line indicating the relationship is converted into the Cartesian coordinate system (x-, y-, and z-axes). In addition, the brain connectivity analysis system 1 computes the dot product of each line of the relationship between the seed channel and other channels on the three coordinate axes (x-, y-, z-axes) of connectivity features (for example, correlation strength, delay time, and physical distance) (FIG. 13). Since the signal from the seed channel (region) is not correlated with the signal per se, the total dot products 1302 are n×(n−1).

From such dot products, distribution histograms 1304a and 1304b (also referred to as global connectivity motifs) are generated and drawn for individual personal data or data on groups 1303a and 1303b. In addition, distribution patterns 1305a and 1305b that approximate the distribution histograms 1304a and 1304b, respectively, are also displayed.

Combining all connectivity features using dot products as described above can simplify the 3D circle plot for each seed channel (region) into a single distribution graph or global connectivity motif, and display it. While analyzing a single seed channel seems to be practical, the analysis may be limited depending on variations of subjects in many cases, and the analysis robustness is also questioned. Therefore, the analysis in the present disclosure provides a global connectivity motif by integrating the connectivity features of a seed channel. Through analysis of the features of the graph shown by the global connectivity motif, the personal and group data can be evaluated with more variables. Such variables can potentially become biomarkers.

<Exemplary Configuration of Inference Analysis Display>

Figure 14:
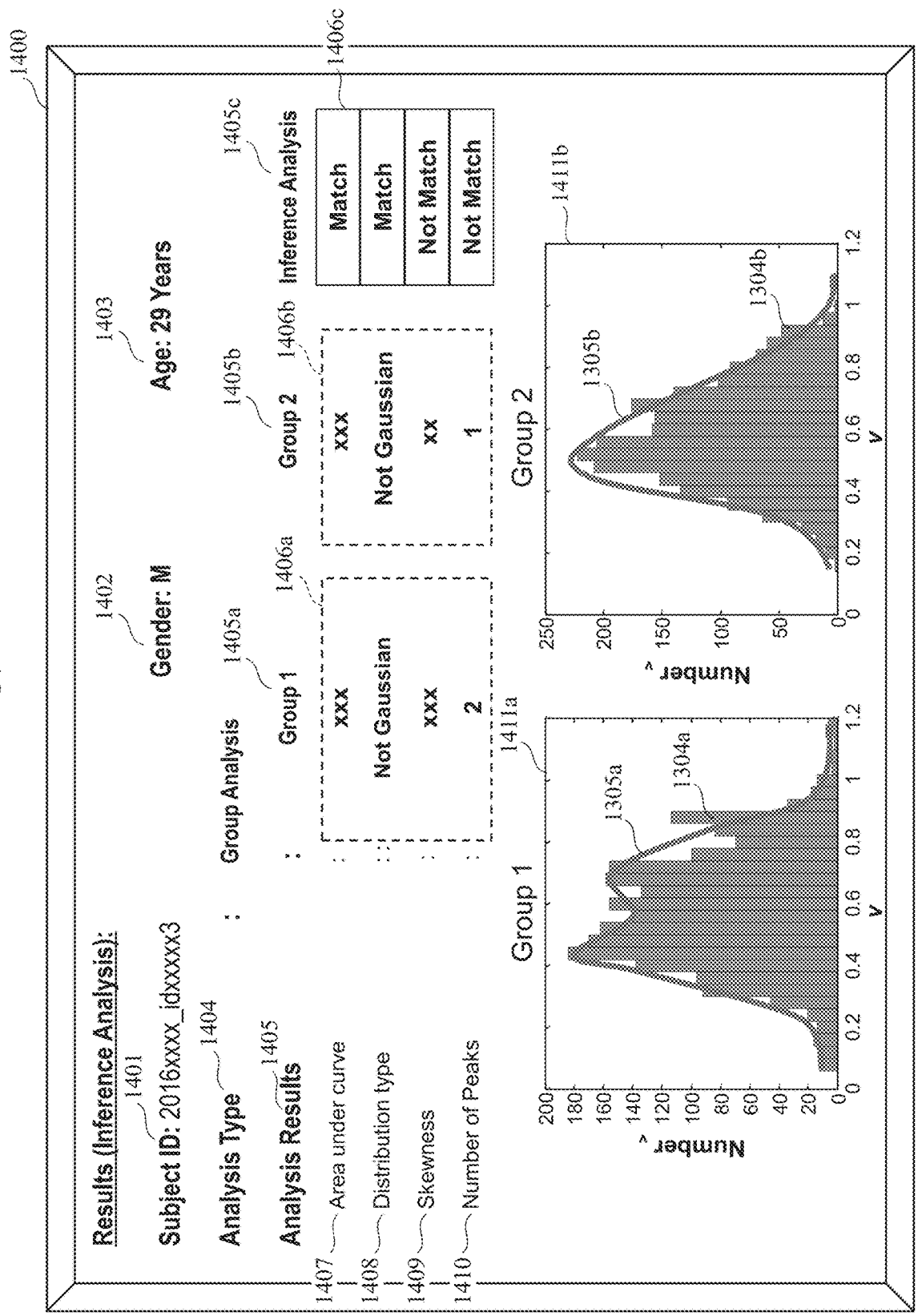
FIG. 14 is a diagram showing an exemplary configuration of a window of an inference analysis display (analysis result display) 1400.

FIG. 14 is a diagram showing an exemplary configuration of a window of an inference analysis display (analysis result display) 1400. The inference analysis display (analysis result display) 1400 can display the results of personal analysis or comparison analysis of a plurality of measured data on groups. FIG. 14 shows the results of group analysis as an example. It should be noted that the processor 11, for example, can be a subject that displays or draws information for the inference analysis display 1400.

The inference analysis display 1400 contains as constituent items the subject ID 1401, gender 1402, age 1403, analysis type 1404, analysis results 1405, and group feature display 1411 (graphs 1411a and 1411b are shown in FIG. 14).

If the number of subjects is more than one, information on the subject ID 1401, gender 1402, and age 1403 is displayed in a corresponding number. Furthermore, a summary of an analysis command is displayed as the analysis type 1404. In FIG. 14, "Group Analysis" is displayed as the analysis type 1404.

The analysis result 1405 is a display area of the main information. In the area 1405, the analysis results for each group (a group 1_1405a and a group 2_1405b in FIG. 14) are visualized with information on the inference analysis 1405c. If personal analysis and not group analysis is performed, the fields of the group 2_1405b and the inference analysis 1405c are not displayed since there is no data on other groups to be compared.

In the analysis methods 1407 to 1410, information corresponding to a designated analysis method is displayed in response to the command 308b input by the operator. The analysis methods used herein include analyses of the area under the distribution curve (area under curve) 1407, distribution type 1408, skewness 1409, the number of peaks 1410, and the like. In particular, analysis of the area under the distribution curve (area under curve) in group/comparison analysis significantly depends on the number channels (regions) selected and/or measured for analysis. That is, if there is a mismatch in the number of channels (regions) between two group data, the global connectivity motifs are normalized separately. After the normality of the distribution type 1408 is assessed, inference made through analysis of the area under the distribution curve (area under curve) 1407 is statistically drawn. Meanwhile, if the distribution of each global connectivity motif is not standard normal (that is, Gaussian distribution), t-, z-, and f-tests should not be performed lightly because the assumed hypothesis (the aforementioned null hypothesis $H_0$) is a hypothesis under normal distribution. Therefore, after the normality is assessed, a statistical test for means, variances, or the like of the two groups is executed on data on the results of normality assessment, resulting in the inference of significant differences between the two groups. If the two groups are not significantly different, the inference analysis 1405c indicates "Match," and if the two groups are significantly different, the inference analysis 1405c indicates "Not Match." The results for each analysis method and the two groups are shown in regions 1406a and 1406b, respectively, and the results of the inference analysis for each analysis method are shown in a region 1406c.

If the distribution type 1408 is selected as the analysis method, for example, normality assessment is executed to distinguish the distributions of the two groups, that is, whether the distributions are Gaussian or other distributions such as Poisson or Log-normal distribution. If the two groups have similar distributions, the inference analysis 1405c indicates "Match." If the skewness 1409 is selected, for example, several statistical tests are executed. Furthermore, if the number of peaks 1410 is selected, the number of peaks generated in each graph of the global connectivity motif is counted. Regardless of which analysis method is selected, the results of the inference analysis 1405c of the two groups are shown in the region 1406c.

As described above, the inference analysis display (analysis result display) 1400 displays the data selected by an operator and the results of analysis (including inference analysis) on the same window. Therefore, the operator can easily analyze the measured data and appropriately conduct diagnosis and the like on the basis of the results of the analysis method selected by him/her.

It should be noted that the distribution map of clustering coefficients (FIG. 11), the global connectivity motif (FIG. 13), the information transfer and a delay time at that time (FIG. 15 or 16), and the like may also be displayed on a window(s) separate from the inference analysis display (analysis result display) 1400, for example.

CONCLUSION (1) In this embodiment, the brain connectivity analysis system acquires from a measurement database measured data on a plurality of channels of a brain (regions: a plurality of channels of a subject selected by an operator), determines at least one of the plurality of channels as a seed channel, and calculates a plurality of connectivity features (for example, correlation strength, information transfer delay time, physical distance, and information transfer direction) between the seed channel and other channels from the measured data. In addition, the system generates a connectivity feature graph (a 2D circle plot or a 3D circle plot: see FIG. 12) showing the relationship between the information transfer delay time and another connectivity feature (for example, the correlation strength or physical distance) of each channel among the calculated connectivity features, and displays the graph on a screen of the display device. Accordingly, the relationship between the channels (regions) can be easily understood and brain connectivity can be comprehensively understood (so far, it has been only possible to understand a specific relationship between regions). Further, if a doctor or the like sees such a graph, it is possible to identify a potential mental disorder of the subject. Further, the brain connectivity analysis in accordance with the present disclosure is independent of an analysis model unlike the conventional analysis, and analysis is performed using only measured data. Therefore, data on a subject can be analyzed flexibly.

In addition, the brain connectivity analysis system converts a line indicating the relationship between connectivity features on a 3D circle plot into the Cartesian coordinates and computes the dot product of each line to generate a distribution histogram and a distribution pattern of the connectivity features and display them (see FIG. 13 or 14). For example, comparing (for example, comparing the shape of) a distribution histogram or pattern of an individual subject with a reference distribution histogram or pattern (for example, a mean of a population) can easily determine if the brain function of the subject is within the normal range. Further, comparing distribution histograms and distribution patterns of a plurality of groups (for example, comparing them by gender, age, disorder, or medication) can understand the tendency of each group.

Further, the brain connectivity analysis system displays the analysis results obtained through analysis of measured data on a plurality of subject groups based on at least one of the analysis methods (analyses of the area under the distribution curve (area under curve), distribution type, skewness, kurtosis, and the number of peaks) for the aforementioned distribution histograms or distribution patterns, and inference analysis information indicating if the analysis results of the plurality of subject groups indicate "Match," together with the distribution histograms and the distribution patterns (see FIG. 14).

(2) The brain connectivity analysis system in this embodiment uses the average value of measured data on a plurality of trials for calculating connectivity features. Alternatively, the brain connectivity analysis system calculates a plurality of connectivity features using measured data on each of a plurality of trials. In addition, the brain connectivity analysis system, when using measured data on a plurality of trials, evaluates the equality of the measured data, and executes a trimming process of eliminating measured data that has been determined as noise-prone measured data on the basis of the percentage of trimming included in an operator's command, and then calculates a plurality of connectivity features using the measured data after the trimming process. If the average value is used, simpler analysis is possible. Meanwhile, if data on each trial is used, more correct analysis is possible because even if measured data on a plurality of trials contains noise, analysis is performed with noise-prone measured data removed.

(3) The present disclosure can also be realized by a program code of software that implements the function of the embodiment. In such a case, a storage medium having recorded thereon the program code is provided to a system or an apparatus, and a computer (or a CPU or a MPU) in the system or the apparatus reads the program code stored in the storage medium. In this case, the program code itself read from the storage medium implements the function of the aforementioned embodiment, and the program code itself and the storage medium having recorded thereon the program code constitute the present disclosure. As the storage medium for supplying such a program code, for example, a flexible disk, CD-ROM, DVD-ROM, a hard disk, an optical disc, a magneto-optical disc, CD-R, a magnetic tape, a nonvolatile memory card, ROM, or the like is used.

Further, based on an instruction of the program code, an OS (operating system) running on the computer or the like may perform some or all of actual processes, and the function of the aforementioned embodiment may be implemented by those processes. Furthermore, after the program code read from the storage medium is written to the memory in the computer, the CPU or the like of the computer may, based on the instruction of the program code, perform some or all of the actual processes, and the function of the aforementioned embodiment may be implemented by those processes.

Moreover, the program code of the software that implements the function of the embodiment may be distributed via a network, and thereby stored in storage means such as the hard disk or the memory in the system or the apparatus, or the storage medium such as CD-RW or CD-R, and at the point of use, the computer (or the CPU or the MPU) in the system or the apparatus may read the program code stored in the storage means or the storage medium and execute the program code.

Finally, it should be appreciated that the process and technology described herein may be implemented substantially by any suitable combination of components without being related to a specific device. Further, a variety of types of general-purpose devices can be used in accordance with the teaching described herein. It may be found to be advantageous to construct a dedicated device to execute the steps of the method described herein. In addition, various inventions can be formed by appropriately combining a plurality of components disclosed in the embodiment. For example, some of the components shown in the embodiment may be removed. Further, the components in different embodiments may be appropriately combined. Although the present disclosure has been described with reference to specific examples, such examples are shown not for limiting purposes but for explanation purposes in all aspects. Those skilled in the art may appreciate that there are a number of combinations of hardware, software, and firmware that are suitable for implementing the present disclosure. For example, the software described herein may be implemented by an assembler or a wide range of programs or script languages such as C/C++, perl, Shell, PHP, or Java (registered trademark).

Further, in the aforementioned embodiment, the control lines and information lines represent those that are considered to be necessary for the description, and do not necessarily represent all of the control lines and information lines that are necessary for a product. Thus, in practice, almost all of the elements may be mutually connected.

Additionally, other implementations of the present disclosure will be apparent to those skilled in the art from consideration of the specification and embodiment of the present disclosure disclosed herein, and the spirit and scope of the present disclosure are shown by the appended claims.

DESCRIPTION OF SYMBOLS

1 Brain connectivity analysis system
11 Processor
12 Program memory
13 Input unit
14 Storage unit
15 Output unit
16 Memory
20 Measurement probe
21 A plurality of light sources
22 A plurality of detectors
23 Measurement point channel
30, 40, 50, 60 Command input screen
301 Analysis type
302 Data selection 303 Data list
307 Connectivity motif analysis selection
501 Analysis level
502 Channel selection
603 Noise trimming selection portion
1400 Inference analysis display (analysis result display)

What is claimed is:

1. A brain connectivity analysis system for analyzing connectivity between regions of a brain, comprising:
a memory configured to have stored therein at least one program including a connectivity analysis program for analyzing the connectivity; and
a processor configured to execute the at least one program stored in the memory to perform the steps of:
acquiring from a storage unit measured data on a plurality of selected regions of a brain;
determining at least one of the plurality of regions as a seed region and calculating a plurality of connectivity features for the seed region and another region from the measured data on the plurality of regions; and
generating a connectivity feature graph showing a relationship between a transfer delay time and another connectivity feature of each region that are included in the plurality of connectivity features,
wherein the processor is configured to further perform the step of identifying an appearance timing of a signal in each of the seed region and the other region, and calculate a transfer delay time in each region,
wherein the connectivity feature graph is generated by selecting one region of the plurality of regions as a first seed region and calculating transfer delay times between the first seed region and other regions of the plurality of regions and selecting another region of the plurality of regions as a second seed region and calculating transfer delay times between the second seed region and other regions of the plurality of regions,
wherein the first or second seed region is estimated to be a source region with respect to the other regions that have longer delay times than the first or second seed region, respectively, and which are considered to be target regions of the first or second seed region, respectively, and
wherein the first and second seed region is estimated to be a target region with respect to the other regions that have shorter delay times than the first or second seed region, respectively, and which are considered to be source regions of the first or second seed region, respectively.

2. The brain connectivity analysis system according to claim 1, wherein the processor is configured to further perform the step of calculating, as the plurality of connectivity features, a correlation strength between the regions, a distance between the regions, and an information transfer direction between the regions in addition to the transfer delay time.

3. The brain connectivity analysis system according to claim 1,
wherein:
the connectivity feature graph is one of a two-dimensional or three-dimensional circle plot, and
the processor is configured to further perform the steps of converting a line indicating a relationship between connectivity features on the connectivity feature graph into Cartesian coordinates and compute a dot product of each line to generate a distribution histogram and a distribution pattern of the connectivity features, and outputting the distribution histogram and the distribution pattern.

4. The brain connectivity analysis system according to claim 3, wherein the processor is configured to further perform the steps of generating the plurality of connectivity features using measured data on an individual subject or measured data on a plurality of subject groups in response to an input command, and generating the connectivity feature graph.

5. The brain connectivity analysis system according to claim 4, wherein the processor is configured to, when the measured data on the plurality of subject groups is used, further perform the step of comparing distribution histograms and distribution patterns of connectivity features of the subject groups and display results of the comparison.

6. The brain connectivity analysis system according to claim 5, wherein the processor is configured to further perform the step of displaying analysis results obtained through analysis of the measured data on the plurality of subject groups using at least one designated analysis method for at least one of the distribution histogram or the distribution pattern, and inference analysis information indicating if the analysis results of the measured data on the plurality of subject groups match, together with the distribution histogram and the distribution pattern.

7. The brain connectivity analysis system according to claim 1, wherein the processor is configured to further perform the step of calculating an average value of measured data on a plurality of trials and calculate the plurality of connectivity features using the average value.

8. The brain connectivity analysis system according to claim 1, wherein the processor is configured to further perform the step of calculating the plurality of connectivity features using measured data on each of a plurality of trials.

9. The brain connectivity analysis system according to claim 8, wherein the processor is configured to further perform the steps of evaluating equality of the measured data on the plurality of trials in response to an input command, executing a trimming process of eliminating measured data that has been determined as noise-prone measured data on the basis of a percentage of trimming included in the command, and calculating the plurality of connectivity features using the measured data after the trimming process.

10. In a brain connectivity analysis system for analyzing connectivity between regions of a brain having a memory configured to have stored therein at least one program including a connectivity analysis program for analyzing the connectivity and a processor configured to execute the at least one program stored in the memory, a method performed by the processor comprising the steps of:
reading a connectivity analysis program for analyzing the connectivity from a memory and executes the program to acquire from a storage unit measured data on a plurality of selected regions of the brain;
determining at east one of the plurality of regions as a seed region and calculating a plurality of connectivity features for the seed region and another region from the measured data on the plurality of regions; and
generating a connectivity feature graph showing a relationship between a transfer delay time and another connectivity feature of each region that are included in the plurality of connectivity features,
wherein the processor is configured to further perform the step of identifying an appearance timing of a signal in each of the seed region and the other region, and calculate a transfer delay time in each region, wherein the connectivity feature graph is generated by selecting one region of the plurality of regions as a first seed region and calculating transfer delay times between the first seed region and other regions of the plurality of regions and selecting another region of the plurality of regions as a second seed region and calculating transfer delay times between the second seed region and other regions of the plurality of regions, wherein the first or second seed region is estimated to be a source region with respect to the other regions that have longer delay times than the first or second seed region, respectively, and which are considered to be target regions of the first or second seed region, respectively, and wherein the first and second seed region is estimated to be a target region with respect to the other regions that have shorter delay times than the first or second seed region, respectively, and which are considered to be source regions of the first or second seed region, respectively.

11. The brain connectivity analysis method according to claim 10,
wherein:
the connectivity feature graph is a two-dimensional or three-dimensional circle plot, and
the method further comprises the steps of converting a line indicating a relationship between the connectivity features on the connectivity feature graph into Cartesian coordinates, computing a dot product of each line to generate a distribution histogram and a distribution pattern of the connectivity features, and outputting the distribution histogram and the distribution pattern.

12. The brain connectivity analysis method according to claim 11, the method further comprising the steps of generating the plurality of connectivity features using measured data on an individual subject or measured data on a plurality of subject groups in response to an input command, and generating the connectivity feature graph.

13. The brain connectivity analysis method according to claim 12, further comprising the steps of, when the measured data on the plurality of subject groups is used, comparing distribution histograms and distribution patterns of connectivity features of the subject groups and displaying results of the comparison.

14. The brain connectivity analysis method according to claim 13, further comprising the step of displaying display analysis results obtained through analysis of the measured data on the plurality of subject groups using at least one designated analysis method for at least of one of the distribution histogram or the distribution pattern, and inference analysis information indicating if the analysis results of the measured data on the plurality of subject groups match, together with the distribution histogram and the distribution pattern.

* * * * *